United States Patent
Postal et al.

(10) Patent No.: US 6,409,507 B1
(45) Date of Patent: *Jun. 25, 2002

(54) DRIVE MECHANISM FOR OSCILLATORY DENTAL TOOL WITH IMPROVED BUSHING

(75) Inventors: Robert T. Postal, Glen Cove; Robert P. Wallace, Amawalk, both of NY (US)

(73) Assignee: Twist2It, Inc., Woodside, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/678,802

(22) Filed: Oct. 3, 2000

Related U.S. Application Data

(63) Continuation-in-part of application No. 09/288,764, filed on Apr. 8, 1999, now Pat. No. 6,247,931, which is a continuation-in-part of application No. 08/878,995, filed on Jun. 19, 1997, now Pat. No. 5,931,672.

(51) Int. Cl.$^7$ .................................................. A61C 3/03
(52) U.S. Cl. ......................................... 433/118; 433/122
(58) Field of Search ............................. 433/118, 122, 433/123, 124, 125

(56) References Cited

U.S. PATENT DOCUMENTS

| | | |
|---|---|---|
| 656,124 A | 8/1900 | Kinnison |
| 1,042,449 A | 10/1912 | Kelchner |
| 1,182,187 A | 5/1916 | McEldowney |
| 1,982,336 A | 11/1934 | Wiseman |
| 2,135,933 A | 11/1938 | Blair |
| 2,389,232 A | 11/1945 | Conlon |
| 2,400,912 A | 5/1946 | Britt et al. |
| 2,451,706 A | 10/1948 | Aimes |
| 2,514,142 A | 7/1950 | Reid |
| 2,706,969 A | 4/1955 | Bannister et al. |
| 3,769,707 A | 11/1973 | Condon |
| 4,099,448 A | 7/1978 | Young |
| 4,272,229 A | 6/1981 | Pape |
| 4,371,341 A | 2/1983 | Nakanishi |
| 4,460,341 A | 7/1984 | Nakanishi |
| 5,040,978 A | 8/1991 | Falcon et al. |
| 5,120,220 A | 6/1992 | Butler |
| 5,145,369 A | 9/1992 | Lustig et al. |
| 5,340,310 A | 8/1994 | Bifulk |
| 5,931,672 A | 8/1999 | Postal et al. |
| 6,247,931 B1 * | 6/2001 | Postal ........................ 433/118 |

OTHER PUBLICATIONS

U.S. application No. 09/288,764, Filed Apr. 4, 1999; Postal.

* cited by examiner

*Primary Examiner*—Ralph A. Lewis
(74) *Attorney, Agent, or Firm*—Handal & Morofsky

(57) ABSTRACT

A transmission for changing rotary motion into angularly reciprocating motion and adapted to be mounted on the output end of a dental power unit of the type having a rotary drive output and used to drive a dental tool. The transmission is comprised of a support member, a driving resinous member supported by the support member for rotary motion, and a driven resinous member supported by the support member for reciprocating angular movement by the support member. The transmission subassembly is formed by the driving resinous member, driven resinous member and support member and adapted to be mounted on the output end of the dental power unit with a rotary drive output mechanically coupled to the driving resinous member. A driving cam surface is disposed on a portion of the driving resinous member. A driven cam surface is disposed on a portion of the driven resinous member. The driving cam surface is in contact with the driven cam surface during at least a portion of the cycle of rotation of the driving cam surface. The driven cam surface is configured and dimensioned to be driven by the driving cam surface in a positive angular direction during one part of the cycle and is driven by the driving cam surface in a negative angular direction during another part of the cycle. Angularly reciprocating motion is thereby imparted to the dental tool as the driving cam surface and driven cam surface engage each other.

13 Claims, 16 Drawing Sheets

Figue 26

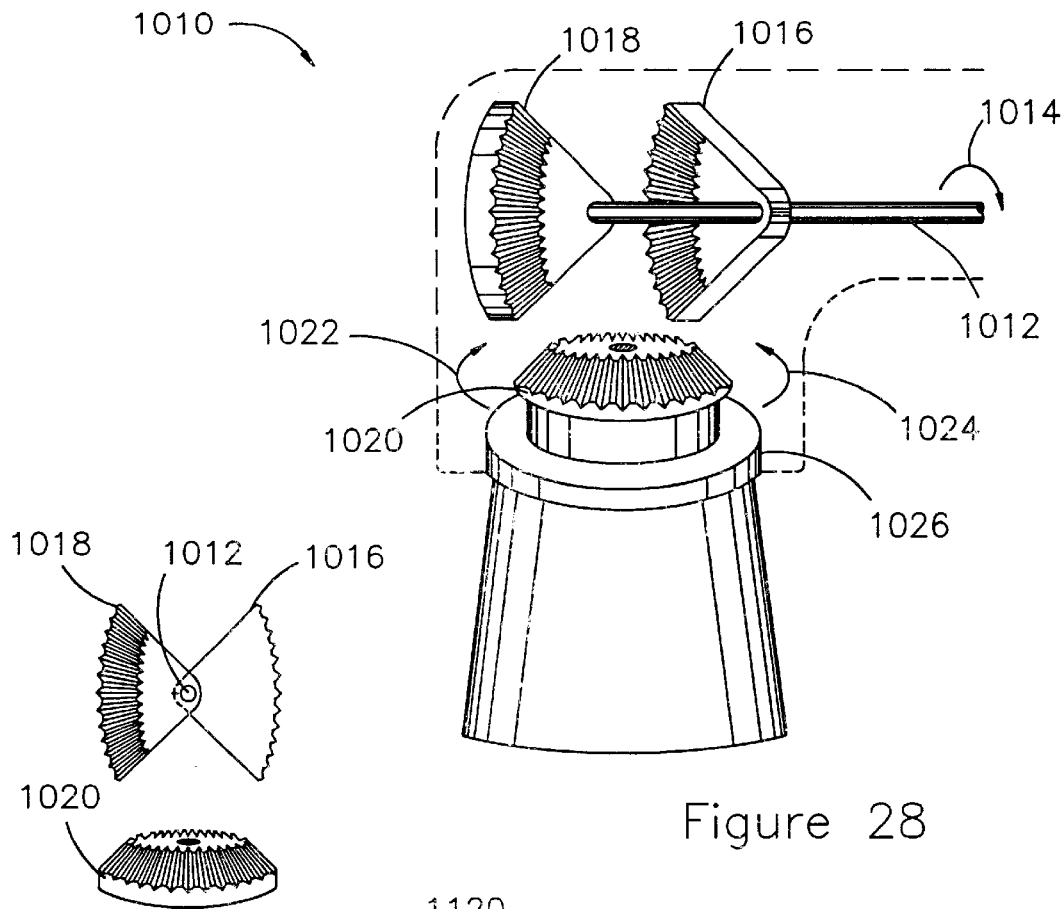
Figure 28
Figure 29
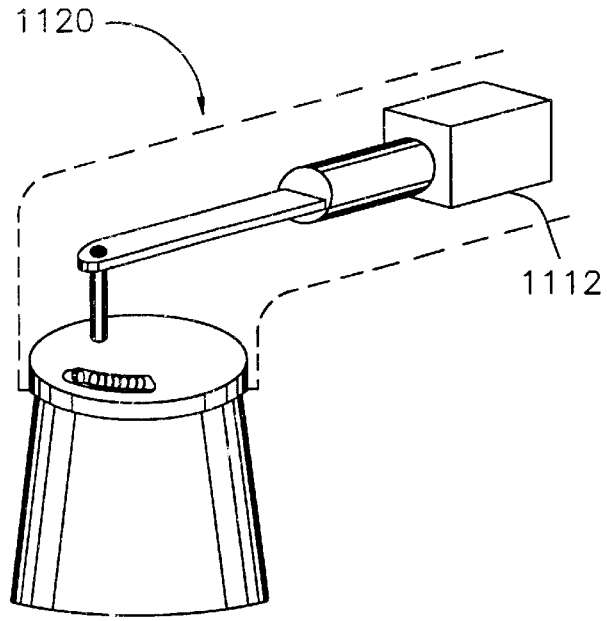
Figure 30

DRIVE MECHANISM FOR OSCILLATORY DENTAL TOOL WITH IMPROVED BUSHING

CROSS-REFERENCE TO RELATED APPLICATIONS

This application is a continuation-in-part of Postal et al. U.S. application Ser. No. 09/288,764, filed Apr. 8, 1999 now U.S. Pat. No. 6,247,931 B1 which is a continuation-in-part of Postal et al. U.S. application Ser. No. 08/878,995, filed Jun. 19, 1997, now U.S. Pat. No. 5,931,672. The disclosures of patents 6,247,931 B1 and 5,931,672 are hereby incorporated herein by reference.

STATEMENT REGARDING FEDERALLY SPONSORED RESEARCH OR DEVELOPMENT

Not Applicable

BACKGROUND OF THE INVENTION

1. Technical Field

The present invention relates to a dental tool assembly having a head that imparts oscillatory motion to a desired dental treatment device coupled to the assembly. More particularly, the present invention relates to a drive mechanism for a dental tool assembly, the drive mechanism having a rotating drive shaft that engages a first end of a driven shaft to rotate the driven shaft in an oscillatory manner. The present invention also relates to a bearing assembly for a dental tool drive mechanism, the bearing assembly supports the drive shaft for rotary motion using a bushing shape to reduce friction while also aligning the drive shaft. A dental tool is coupled to a second end of the driven shaft and is thereby rotationally oscillated.

2. Description of the Related Art

Dental tool assemblies, such as prophy angles and drills, which impart an oscillatory rotary motion to a dental treatment device coupled thereto are known in the art. In particular, such assemblies typically have a driving mechanism comprising a drive shaft with a rotation axis that is perpendicular to the rotation axis of a driven shaft to which the dental treatment device is coupled. The drive shaft of prior art driving mechanisms has an element positioned eccentric to its rotation axis and extending towards the driven shaft to engage a slot in the driven shaft. Rotation of the drive shaft thus imparts an oscillatory rotation to the driven shaft.

For example, U.S. Pat. No. 1,711,846 to Heilbom shows a dental filing device having a drive shaft perpendicularly oriented with respect to a file holder. A crank pin, mounted on a crank disc on an end of the drive shaft adjacent the file holder, engages within a bore in the file holder. The crank pin is positioned on the crank disc eccentric to the rotation axis of the drive shaft. Thus, rotation of the drive shaft rotates the eccentrically positioned stud, thereby causing the file holder to rotate in an oscillatory manner.

Similarly, the dental instrument in U.S. Pat. No. 2,135,933 to Blair has a rotary drive shaft with an eccentrically positioned stud that engages within a slot of a piston to which a massage tip is coupled. Rotation of the drive shaft causes oscillatory rotation of the massage tip. Another massage tool that imparts oscillatory motion to a head spindle to which a massage cup or brush is coupled is shown in U.S. Pat. No. 4,534,733 to Seigneur in et al. In the Seigneur in Patent, the stud that engages the head spindle is mounted eccentric to the rotation axis of the drive shaft, but is inclined to extend across the rotation axis. The portion of the stud that is aligned with the rotation axis of the drive shaft is also aligned with the rotation axis of the head spindle. The dental tool shown in U.S. Pat. No. 4,460,341 to Nakanishi also has a guide pin mounted eccentric to the rotation axis of a drive shaft and engaging within a slot of a driven shaft to which a dental treatment device is coupled.

In all of the above-described dental tool assemblies, a stud or pin extends into a slot to drive the element to which the dental treatment device is coupled. Because the treatment device typically must be driven at very high speeds (e.g., the recommended speed of a standard prophy angle at approximately 6,000 rotations per minute), there is a risk of the stud or pin breaking off during use. Moreover, manufacturing of the drive shaft and driven shaft is complicated by the necessity of forming a stud and a slot that are shaped for ready, secure engagement such that rotation of the drive shaft causes oscillatory rotation of the driven shaft.

Additionally, some of the drive shafts of the above-described patents also impart reciprocatory axial motion to the driven shaft along the longitudinal shaft of the driven shaft. When such axial motion is not desired, the driven shaft should be locked with respect to the housing in which the drive shaft and driven shaft are positioned, and thus locked with respect to the rotation axis of the drive shaft. Typically, such locking is accomplished by locking the driven element with respect to the housing such as by inter-engagement of stepped portions and/or flanges. However, such locking imparts substantial stresses against the housing and driven shaft.

Another drawback of the above-described devices is that they are typically formed from metal and are reusable. The sterilization process necessary in order to reuse the device is typically costly and time consuming. It therefore has been desirable to provide disposable dental tool assemblies that are used only once and therefore need not be sterilized. Such tools typically are made from plastic.

Because plastics are generally not as strong as metals, the driving mechanism used in the above-described devices cannot be used because of the inherent weakness of the stud. Therefore, the driving mechanisms of disposable dental tools typically have interengaging gears, such as shown in U.S. Patent No. 5,571,012 to Witherby et al. Because gears are used, the same reciprocatory rotary motion provided by the non-disposable tools cannot be achieved. However, such oscillating movement is desired for a number of reasons. The back and forth reciprocating motion provided by non-disposable dental tool assemblies permits greater speeds to be used and greater pressure to be applied than rotary type devices that do not oscillate, and also may massage the gums of the patient. Additionally, oscillatory movement generates less heat than a full rotational action. Moreover, the risks of hitting undercuts, cutting or tearing soft tissue, and splattering of agents applied by the treatment tool are reduced if not substantially eliminated.

Another problem faced by any drive mechanism is how to provide support and alignment for the moving parts. There are many types of bearings that may be used for this purpose. Due to the size, construction methods, and materials used in prophy angles, journal or sleeve style bearing configurations are generally used.

An example of such a bearing is shown in U.S. Pat. No. 5,340,310 issued to Bifulk on Aug. 23, 1994. As shown in FIGS. 3, 4 and 5 thereof, a housing having a cylindrical bore with fingers spaced from and extending axially parallel to the bore are provided for receiving a bushing having a square cross-section such that the bushing abuts turned in portions of the fingers. The fingers are flexible such that they bend outwardly allowing the bushing to be pushed past the turned in portions yet bend back to capture the bushing therein.

Another example of a drive mechanism is shown in U.S. Pat. No. 5,931,672 issued to R. Postal on Aug. 3, 1999. The mechanism disclosed therein uses a series of flanges and a latch that includes a position retaining surface that contacts the outer periphery of at least one of the flanges. The extreme outer edge of the flanges provide axial alignment for the drive shaft.

In use, this arrangement is susceptible to heat build-up on the various bearing surfaces. This problem is compounded by the difficulty in lubricating the bearing surfaces during assembly of the components. Therefore it is desirable to have a bearing surface that is less susceptible to heat build-up and is easily lubricated during assembly. It is also desirable to have a bearing arrangement that is less complex to assemble. The present invention addresses these desires for improving the bearing arrangement in prophy angle drive mechanisms.

BRIEF SUMMARY OF THE INVENTION

It is therefore an object of the present invention to provide a disposable dental tool assembly having a driving mechanism that imparts oscillatory rotary motion to a dental treatment device mounted on the assembly and to achieve this with a structure that can be economically, and reliably implemented in plastic to allow for disposability and the attendant avoidance of the spreading of infection.

It is a related object of the present invention to provide a driving mechanism having a drive shaft and a driven shaft each having driving surfaces shaped to engage each other and ride along each other such that rotation of the drive shaft causes oscillatory rotation of the driven shaft.

It is a further object of the present invention to provide a dental tool assembly having driving and driven elements that are stabilized with respect to each other against relative movement in a given direction.

It is another object of the present invention to provide a dental tool assembly having a drive shaft that is coupled to a driven element such that the drive shaft imparts only oscillatory motion to the driven element without also imparting axial motion to the driven element.

These and other objects of the present invention are accomplished in accordance with the principles of the present invention by providing a dental tool assembly having a rotating drive shaft that engages a driven shaft to impart oscillatory rotary motion to the driven shaft. The drive shaft and driven shaft are positioned transverse to each other. The drive shaft has a driving surface at its distal end that is shaped to engage a driven surface on a side of the driven shaft adjacent the drive shaft. Because of the manner in which the distal end is shaped, a stud or guide pin, such as used in the prior art, is no longer needed. Specifically, the driving surface is a cutaway, curved portion of an enlarged end of the drive shaft, and the driven surface is a cut-away side portion of the driven shaft. The cut-away portions of each shaft are shaped to interengage with substantially no play there between such that they are in continuous contact during rotation of the driving shaft. Because of the shapes of the cut-away portions, rotation of the driving shaft causes oscillatory rotation of the driven shaft.

The drive shaft and driven shaft are positioned within a housing. In order to prevent relative movement of the shafts with respect to the housing, a plurality of locking mechanisms are provided. First, the drive shaft is provided with a longitudinally extending pin aligned with the rotation axis of the drive shaft. The driven shaft is provided with a slot through which the pin is passed. The slot is shaped so that oscillatory rotation of the driven shaft is not inhibited by the pin, yet axial movement of the driven shaft along its rotation axis is prevented. Another locking mechanism for the drive shaft is provided in the form of at least one flange extending radially from the drive shaft and engaging a radially inwardly extending flange on the inner surface' of the housing. The driven shaft is provided with a rearwardly positioned pin that fits within a bore in the housing to lock the driven shaft in the desired position for oscillation.

In the alternative, a bearing assembly acting as both a thrust bearing and a retainer for holding the drive shaft in place is characterized in that it includes a bushing having an inwardly facing frustoconical surface acting in concert with a journal attached to the drive shaft and having a contact surface in contact with said frustoconical surface, said bushing also having a snap-fit arrangement on a peripheral surface thereof.

BRIEF DESCRIPTION OF THE SEVERAL VIEWS OF THE DRAWING

These and other features and advantages of the present invention win be readily apparent from the following detailed description of the invention, the scope of the invention being set out in the appended claims. The detailed description will be better understood in conjunction with the accompanying drawing, wherein like reference characters represent like elements throughout the various views of the drawing and:

FIG. 26 is a perspective view of a plastic driving mechanism of the dental tool assembly incorporating a multiple cam driving mechanism;

FIG. 28 is a perspective view of a plastic driving mechanism of the dental tool assembly incorporating a multiple gear driving mechanism;

FIG. 29 is a side view of the multiple gear driving mechanism;

FIG. 30 is a perspective view of a plastic driving mechanism of the dental tool assembly incorporating an electromechanical operator;

DETAILED DESCRIPTION OF THE PREFERRED EMBODIMENTS

Figure 1:
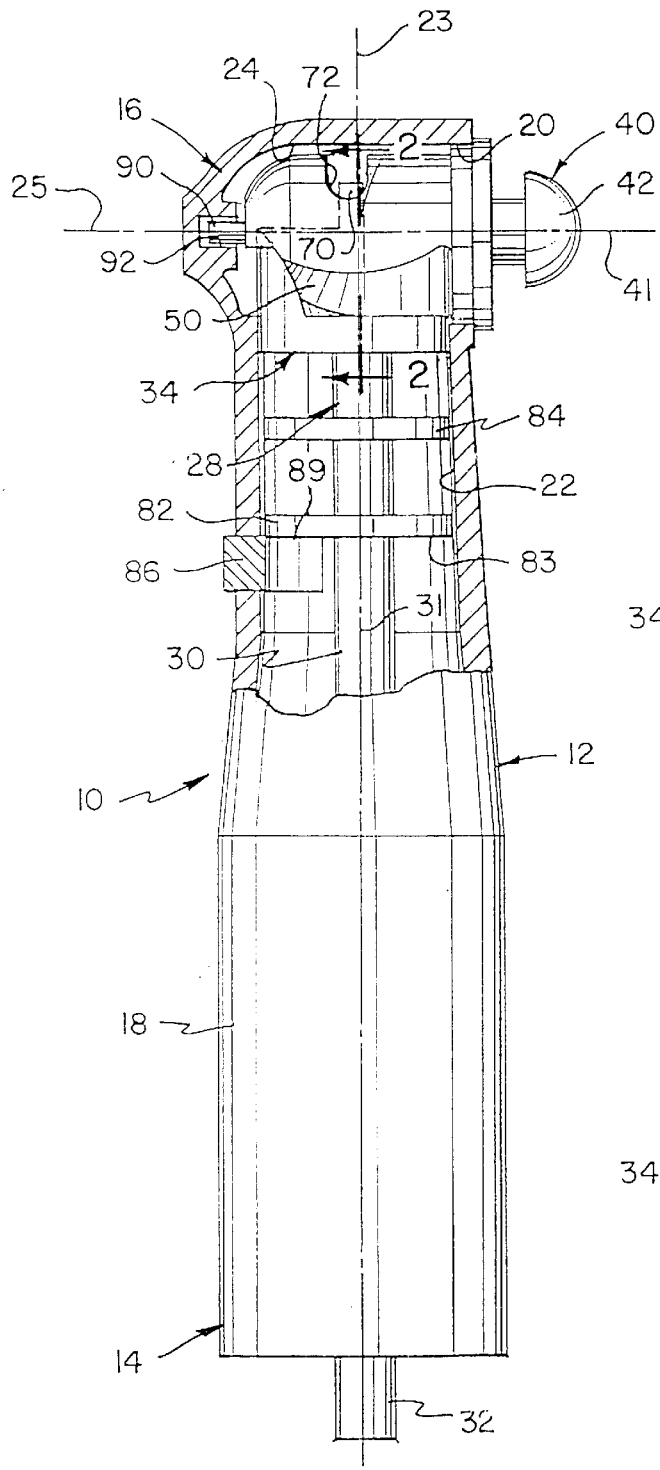
FIG. 1 is an elevational, partially cut-away view of a dental tool assembly formed in accordance with the principles of the present invention.
Figure 2A:
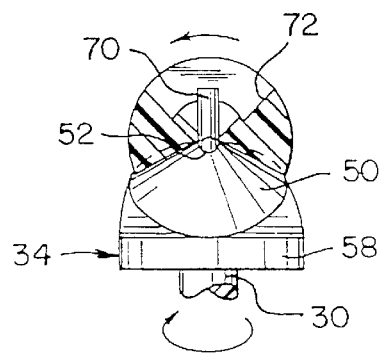
FIG. 2A is a cross-sectional view of the distal end of the dental tool assembly of FIG. 1 along line 2—2, with the driven shaft in the rest position.
Figure 2B:
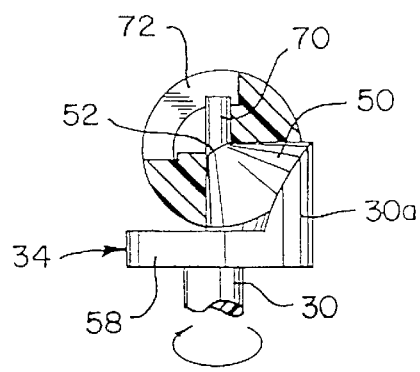
FIG. 2B is a cross-sectional view of the distal end of the dental tool assembly of FIG. 1 along line 2—2 with the drive shaft rotated 90° from the position shown in FIG. 2A.
Figure 3:
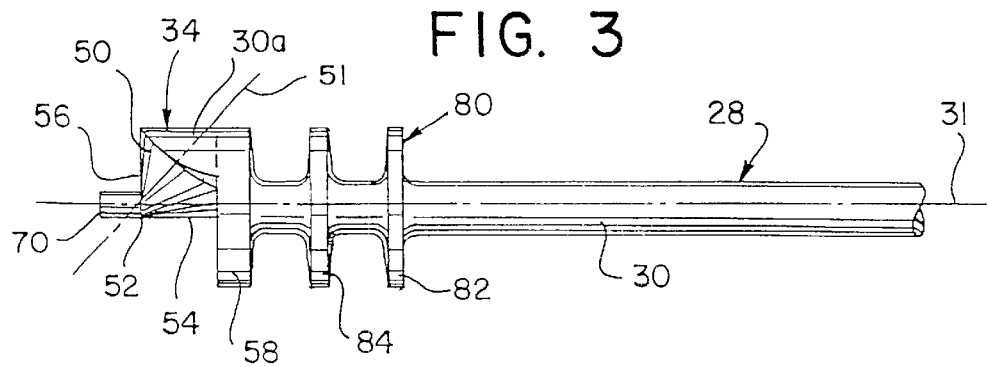
FIG. 3 is an elevational view of a drive shaft formed in accordance with the principles of the present invention.
Figure 4:
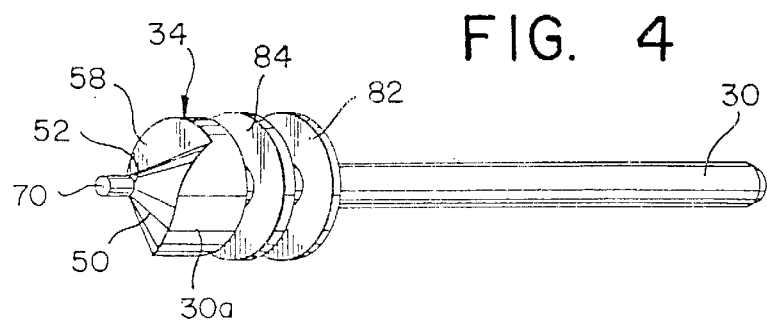
FIG. 4 is a perspective view of the drive shaft of FIG. 2.
Figure 5:
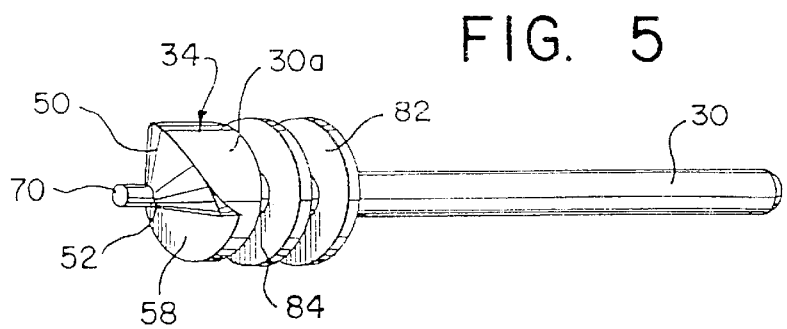
FIG. 5 is a perspective view of the drive shaft of FIGS. 3 and 4, rotated to another position.
Figure 6:
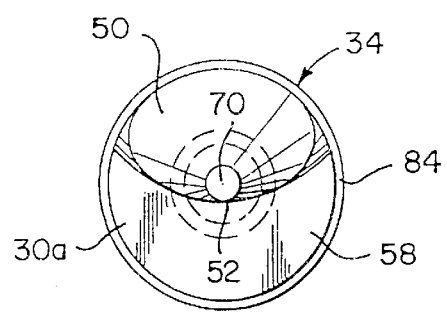
FIG. 6 is an end view of the drive shaft of FIG. 3.

A dental tool assembly 10, formed in accordance with the principles of the present invention, is shown in FIG. 1.

Dental tool assembly 10 includes a housing 12 having a proximal end 14 and a distal end 16, with main body portion 18 extending there between. Proximal end 14 is coupled to a dental tool hand piece (not shown) known in the art. Distal end 16 has a side opening 20 at which a desired dental treatment device (not shown) is coupled. It will be understood that any dental treatment device known in the art may be used. However, the preferred embodiment of the dental tool assembly shown in the FIGS. is a prophy angle to which a prophy cup or brush is coupled to apply prophy paste.

Housing 12 is hollow such that first and second channels 22, 24 are formed therein for housing driving mechanism 28. First, longitudinal channel 22 is formed within main body portion 18 and extends from proximal end 14 to distal end 16 along longitudinal axis 23 of main body portion 18. Second, transverse channel 24 extends across the distal end 16 of housing 12 and opens at side opening 20 of housing 12. Longitudinal axis 25 of transverse channel 24 is transverse and preferably substantially perpendicular to longitudinal axis 23 of housing 12.

Driving mechanism 28 includes a drive shaft 30 and a driven shaft 40. Drive shaft 30 is housed in first channel 22 and has a longitudinal rotation axis 31 which prefer-ably corresponds to longitudinal axis 23 of main body portion 18. A proximal end 32 of drive shaft 30 preferably extends beyond proximal end 14 of housing 12 for connection to a rotary unit (not shown), such as a motor, for rotating drive shaft 30, as known in the art. Distal end 34 of drive shaft 30 extends toward, and preferably partially into, second channel 24. Driven shaft 40 is housed in second channel 24 and has a longitudinal rotation axis 41 which preferably corresponds to longitudinal axis 25 of transverse channel 24. Driven shaft 40 preferably has a coupling element 42 extending therefrom through side opening 20 and out of housing 12. A desired dental treatment device, selected from those known in the art such as a prophy cup or brush, may be coupled to coupling element 42.

Drive shaft 30 and driven shaft 40 have driving surfaces that are shaped to interengage each other to result in a camming action that translates rotation of drive shaft 30 into oscillatory rotation of driven shaft 40 substantially without play between the driving surfaces, as will now be described. As shown in FIGS. 2A, 2B, and 3–6, drive shaft 30 has a drive surface 50 (which functions essentially as a cam) at distal end 34. Preferably drive surface 50 has a substantially conical cam surface, with cone axis 51 being at a preferably 45° angle with respect to rotation axis 31, as may be observed in FIG. 3. The conical shape is readily appreciated with reference to FIGS. 2A, 2B, and 3–6. The tip 52 of conical drive surface 50 preferably is aligned with rotation axis 31 so that a longitudinal surface portion 54 of conical surface 50 is aligned with rotation axis 31 and a transverse surface portion 56 of conical surface 50 is substantially perpendicular, i.e., at a 90° angle, with respect to rotation axis 31 and thus with respect to longitudinal surface portion 54: As may be seen in FIGS. 2B and 3–6, conical surface 50 is formed to one side of rotation axis 31. Conical surface 50 may be formed by cutting away a portion of an enlarged region 30a of shaft 30, thus leaving a flange-like section 58 at distal end 34.

Figure 7:
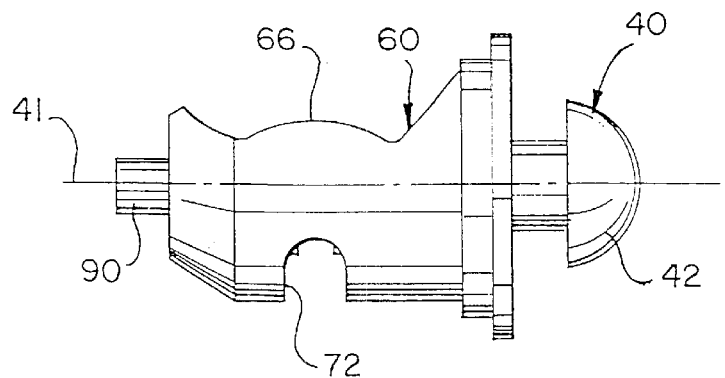
FIG. 7 is an elevational view of a driven shaft formed in accordance with the principles of the present invention.

Driven shaft 40 (which essentially functions as a cam follower), shown in isolation in FIGS. 7–10, has a driven surface 60 along its side (i.e., extending along rotation axis 41 of driven shaft 40). The elevational view of FIG. 7 is similar to the view of driven shaft 40 in FIG. 1, except that driven shaft 40 is shown with driven surface 60 facing upward, rather than downward as in FIG. 1. Typically, driven surface 60 is formed as a cut-away portion of a side of driven shaft 40. Driven surface 60 has alternating hills 62 and valleys 64. Preferably, two hills 62 are provided opposite each other with a valley 64 between adjacent, juxtaposed sides of opposed hills 62, thus spacing hills 62 apart. Viewed another way, the upwardly extending sides of the opposite valleys 64 are joined to form hills 62. Hills 62 and valleys 64 are shaped to conform to the shape of drive surface 50 such that drive surface 50 is in continuous contact with driven surface 60 with substantially no play there between as drive shaft 30 rotates during operation of dental tool assembly 10. Specifically, valleys 64 of driven surface 60 are conically cut-away such that conical drive surface 50 may be engaged therewith such that transverse surface portion 56 and distal surface portions adjoining transverse surface portion 56 of conical drive surface 50 are in close contact with the surfaces of a valley 64. Because opposite sides of conical drive surface 50 are at an approximately 90° angle with respect to each other and valleys 64 are shaped to conform to conical drive surface 50 with hills 62 formed at the sides of valleys 64, peaks 66 of hills 62 are preferably also at an approximately 90° angle with respect to each other. The contour of driven surface 60 may be better understood from a review of the elevational views of FIGS. 8 and 10.

The camming action of the present invention, which permits rotation of drive shaft 30 to cause oscillatory rotation of driven shaft 40 as a result of the interaction of the shapes of driving surfaces 50, 60, will now be described. When drive surface 50 engages a valley 64 of driven surface 60, driven shaft 40 is in a rest position (i.e., driven surface 60 completely faces drive surface 50 and proximal end 14 of housing 12, rather than a side of housing 12, as shown in FIG. 1). As drive shaft 30 rotates about rotation axis 31, drive surface 50 moves along driven surface 60 until drive surface 50 engages a hill 62. As described above, and as may be seen in FIG. 8, the peaks 66 of opposite hills 62 are positioned substantially 180° apart with the bottoms 65 of valleys 64 approximately 90° from each peak 66. Thus, when drive surface 50 has rotated 90° from a rest position in contact with valley 64 (such as shown in cross-sectional view 2A), drive surface 50 comes into contact with adjacent hill 62. When transverse surface portion 56 of drive surface 50 contacts peak 66 of an adjacent hill 62, peak 66 is also transverse to rotation axis 31 such that driven shaft 40 is rotated 90° about its rotation axis 41 from its rest position. It is noted that peaks 66 are at an approximately 90° angle with respect to each other, as may be seen in FIG. 2B, and longitudinal and transverse portions 54, 56 of drive surface 50 are also at an approximately 90° angle with respect to each other, as may be appreciated with reference to FIGS. 1, 2B, and 3. Thus, when transverse portion 56 of drive surface 50 contacts a peak 66 to rotate driven shaft 40, longitudinal portion 54 is in contact with the opposite peak 66. As drive surface 50 continues to be rotated upon rotation of drive shaft 30, drive surface 50 contacts the next valley 64 (opposite the first mentioned valley), returning driven shaft 40 to the rest position. Further rotation of drive shaft 30 brings drive surface 50 into contact with the next hill 62 (opposite the first-mentioned hill), thereby rotating driven shaft 40, in the same manner as described above but in the opposite direction, 90° about rotation axis 41. Thus, driven shaft 40 oscillates a total of 90°, performing a quarter turn in opposite directions from a rest position.

Figure 8:
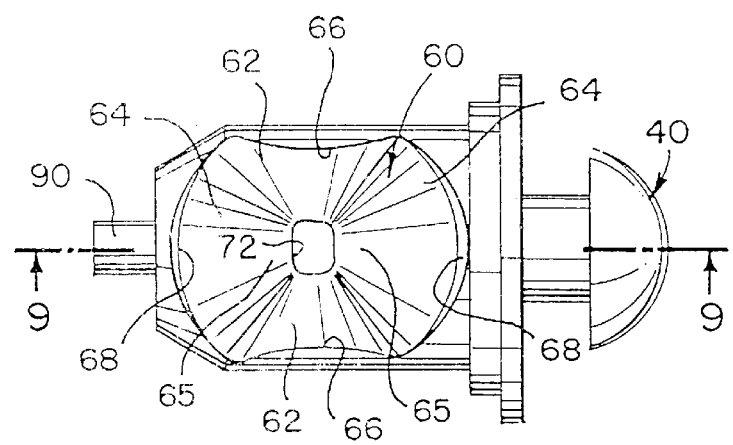
FIG. 8 is a plan view of the driven shaft of FIG. 7.
Figure 9:
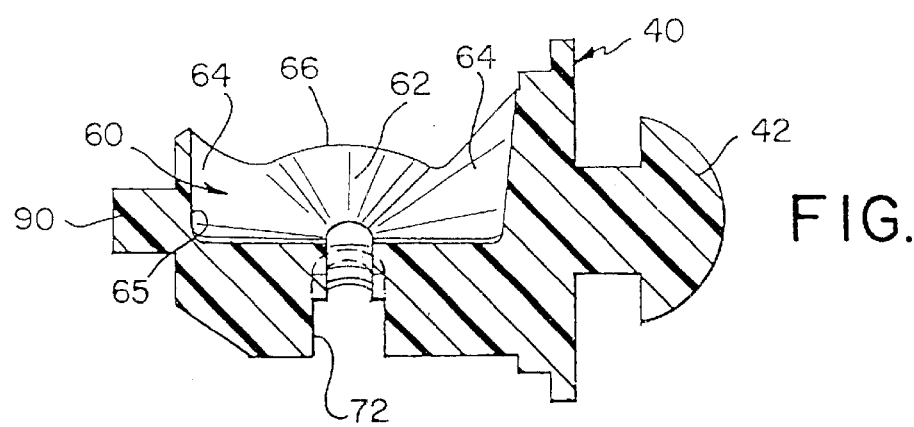
FIG. 9 is a cross-sectional view along line 9—9 of the driven shaft of FIG. 8.
Figure 10:
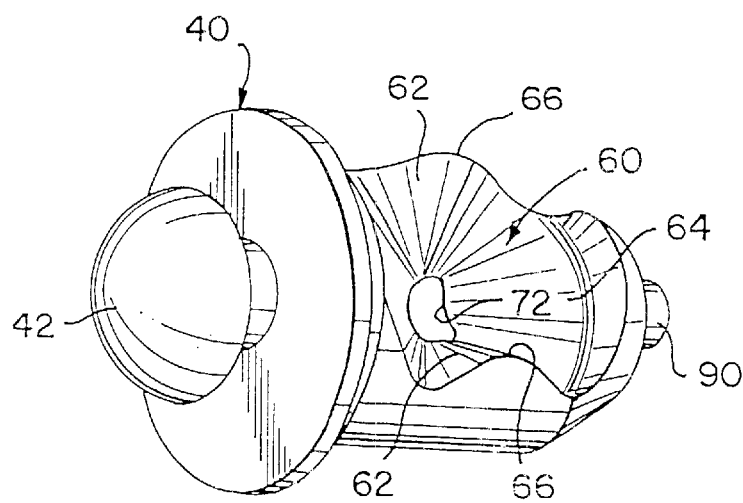
FIG. 10 is a perspective view of the driven shaft of FIGS. 7–9.
Figure 11:
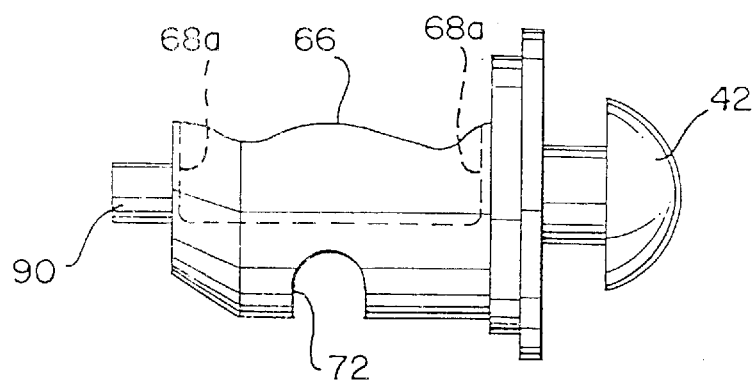
FIG. 11 is an elevational view of a driven shaft similar to that of FIG. 7 but with straight transverse walls of the driven surface.
Figure 12:
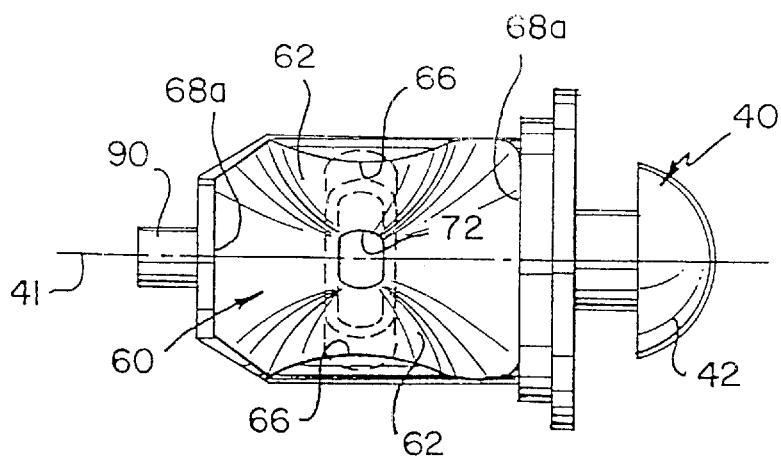
FIG. 12 is a plan view of the driven shaft of FIG. 11.

As may be seen in the plan view of FIG. 8, transverse side walls 68 of driven surface 60 are curved. However, in order to provide greater clearance between side walls 68 and drive shaft 30 (particularly the outer walls of enlarged region 30a extending substantially parallel to rotation axis 31) substantially straight side walls 68a may, instead, be provided, as shown in FIGS. 11 and 12. Straight side walls 68a extend, from the widest portions of valleys 64, along the periphery of driven surface 60 substantially perpendicular to rotation axis 41 of driven shaft 40.

Because typically only oscillatory rotation, without axial reciprocation, of driven shaft 40 is desired, it is desirable to fix drive shaft 30 with respect to driven shaft 40. In accordance with the principles of the present invention, drive shaft 30 is provided with an axially extending pin 70 that is substantially aligned with rotation axis 31. Driven shaft 40 is provided with a corresponding slot 72, which may extend completely through driven shaft 40, as shown in FIGS. 2A, 2B, and 7–10. It will be understood that slot 72 need not extend completely through driven shaft 40, as shown, as long as sufficient engagement between pin 70 and slot 72 is achieved. The axial extent of slot 72 along rotation axis 41 of driven shaft 40 is selected to provide a substantially close fit with the diameter of pin 70 to prevent axial reciprocation of driven shaft 40 along axis 41. However, the transverse extent of slot 72 (in a direction perpendicular to axis 41) is selected such that 90° rotation of driven shaft 40 with respect to drive shaft 30 (45° rotation of driven shaft 40 in each direction from the rest position) is permitted without causing shifting of either shaft 30, 40 from respective axes 23, 25 of housing 12.

In order to prevent movement of shafts 30, 40 from their proper positions within channels 22, 24 of housing 12, position retaining elements are provided as follows. In order to prevent axial shifting of drive shaft 30 along axis 31, drive shaft 30 is provided with at least one radially extending stop flange 80. As shown in FIGS. 1 and 3–5, preferably a proximal flange 82 and a distal flange 84 are provided. Flange 58 may also be considered to perform the same function as that of flanges 82 and 84 and thus may be considered a stop flange 80 as well. Housing 12 is provided with a latch 86 (inserted after assembly in order to maintain the parts of dental tool assembly 10 in place) having a position retaining surface 89 extending radially inwardly from the walls of channel 22. Position retaining surface 89 is positioned adjacent and along a retaining surface 83 of proximal flange 82 to prevent proximal axial movement of drive shaft 30 towards proximal end 14 of housing 12. Additional position retaining surfaces may be provided extending radially inwardly from the inner walls of channels 22 to engage proximal position retaining surfaces on flanges 58 and 84 as well. It will be understood that the position retaining surfaces formed on housing 12 need, not be in the form of a latch, but may be in any other form, such as a radially inwardly extending shoulder, that provides a sufficient surface area for engaging a proximal face of at least one of the flanges 80 on drive shaft 30. Moreover, the position retaining surfaces on housing 12 must be securely fixed to housing 12 along axis 23 to prevent movement of drive shaft 30 along axis 23.

In order to secure axial alignment of driven shaft 40 with axis 25, a positioning pin 90 may be provided at a rear, inner end of driven shaft 40 to fit within bore 92 at a rear end of channel 24 of housing 12, as shown in FIG. 1. Pin 90 not only serves to maintain proper alignment of driven shaft 40 during use, but also facilitates alignment of driven shaft 40 in housing 12 during assembly.

Preferably, to assemble dental tool assembly 10, driven shaft 40 is first positioned in housing 12, with pin 90 fitting within bore 92 such that rotation axis 41 of driven shaft 40 is properly aligned with longitudinal axis 25 of channel 24. Driven shaft 40 is rotated into its rest position such that driven surface 60 faces proximal end 14 of housing 12. Drive shaft 30 may then be inserted into channel 22, with pin 70 extending into slot 72 of driven shaft 40. Latch 86 then is positioned such that position retaining surface 89 faces position retaining surface 83 to maintain drive shaft 30 in its proper position along longitudinal axis 31 of channel 22. Dental tool assembly 10 then is ready for coupling with the desired hand piece.

Figure 13:
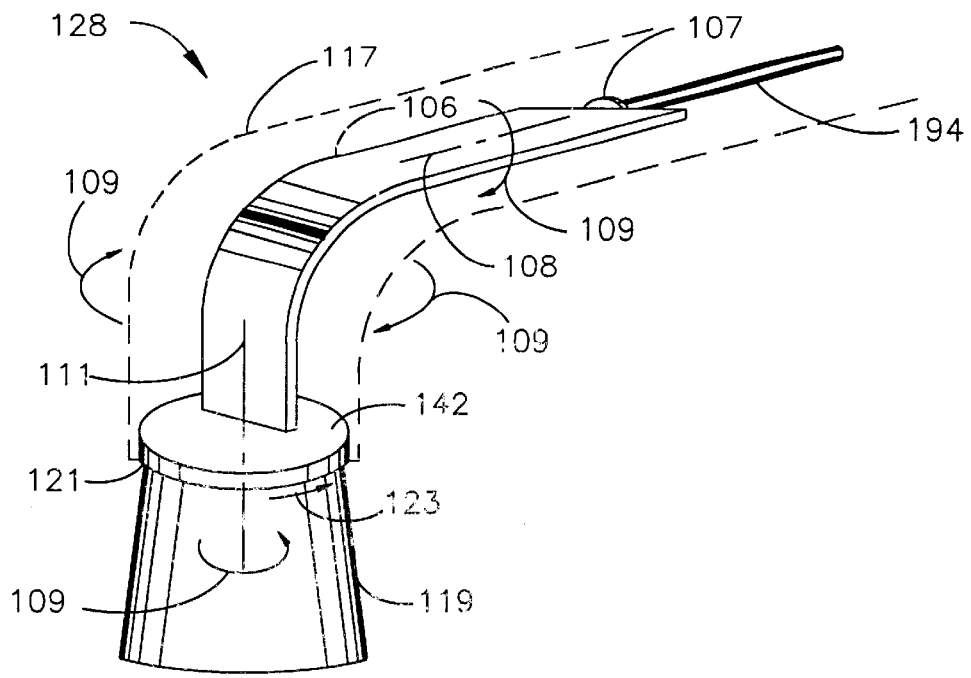
FIG. 13 is a perspective view of a plastic driving mechanism of the dental tool assembly incorporating a flexible driving member.

An alternative embodiment of the present invention is illustrated in FIG. 13. In this embodiment, the inventive plastic driving mechanism 128 is driven by a rotating member 194, which serves as a source of rotary input power. Rotating member 194 is a simple elongated driving shaft, of the same configuration as the driving shaft in a conventional rotating prophy angle, and thus, like the other inventive embodiments of the invention may be easily substituted in existing dental apparatus in wide use at dentist's offices. Rotating member 194 is coupled to a flexible driving member 106 by any suitable coupling 107. During use, flexible driving member 106 is rotated in the direction indicated by arrows 109. The part of flexible driving member 106 closer to rotating member 194 rotates along a horizontal longitudinal oscillatory axis 108. Similarly, the distal portion of flexible driving member 106 rotates along a vertical oscillatory axis 111.

In accordance with this embodiment of the invention, flexible driving member 106 is maintained in a curved configuration. As can be seen in FIG. 13, flexible driving member 106 has a thickness 113 which is much smaller than its width 115. Because of the flexible driving member 106 is maintained in a curved configuration as illustrated in FIG. 13, rotation of the proximal portion of flexible driving member 106 at a constant speed causes a snap in the angular rotation of the distal end of flexible driving member 106.

This irregularity in angular speed amounts to a sort of stall during which gum tissue has an opportunity to resume an unstressed configuration. In many respects, the effect is similar to that achieved by the reciprocating motion of the prophy angle, which stresses the gum tissue in one direction, then reverses direction, relieving the stress and lessening the likelihood of tissue damage that would be more likely if one continued to apply stress and high-speed in one direction, as would be the case in the typical rotary prophy angle drive mechanism.

Flexible driving member 106 is maintained in the curved configuration illustrated in FIG. 13 by housing, the same as in a curved tubular housing 117, which is illustrated in dashed lines in FIG. 13. More particularly, it is noted that in accordance with this embodiment of the invention, a rubber prophy angle 119, which functions as a tooth scrubbing surface and is of conventional design snaps onto a plastic support member 142. Plastic support member 142 is mounted for rotation within a secular mouth 121, which is configured to receive the disk shaped top of member 142, thus securely holding member 142 and allowing only rotation in the direction illustrated by arrow 123, in response to power input to the system by rotary member 194.

The intermittent nature of the motion in the embodiment illustrated in FIG. 13 may be improved by introducing a measure of friction between member 142 and mouth 121.

Figure 14:
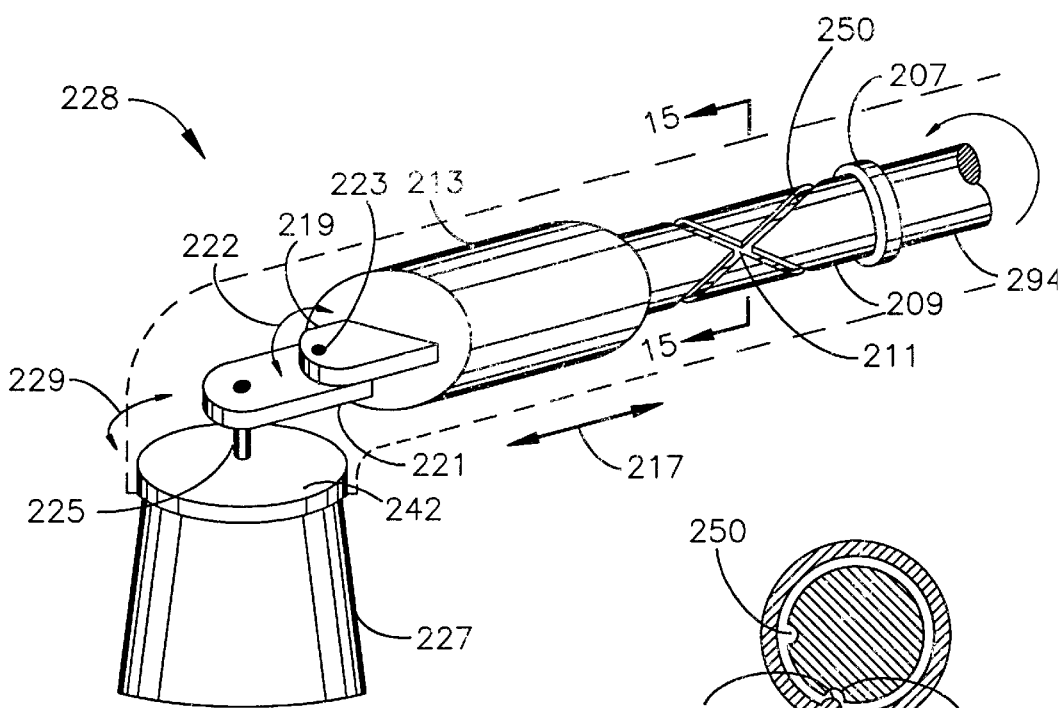
FIG. 14 is a perspective view of a plastic driving mechanism of the dental tool assembly incorporating a cylindrical driving member.
Figure 15:
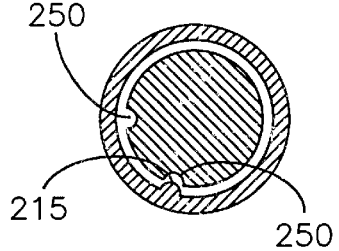
FIG. 15 is a cross-sectional view of the dental tool assembly of FIG. 14 along lines 15.

FIGS. 14 and 15 show an alternative embodiment of the inventive plastic driving mechanism 228. FIG. 14 is partially in exploded perspective as will be apparent from the following description. In this embodiment, plastic driving mechanism 228 is driven by a rotary input 294, of the type conventionally incorporated in a dental tool power source that might be used by a dentist to power a drill or other similar instrument. The output of rotary input 294 is coupled by a coupling mechanism 207 to a cylindrical driving member 209. Cylindrical driving member 209 defines a drive surface 250 comprising a figure-eight shaped groove. As can be seen in FIG. 14, this groove extends around cylindrical driving member 209 twice, crossing over itself at point 211 to define the figure-eight shape. For the sake of clarity of illustration, cylindrical driving member 209 is shown outside of sleeve 213. During operation, cylindrical driving member 209 is positioned within sleeve 213. Sleeve 213 has secured within it a cam following nub 215 which is positioned within groove-shaped drive surface 250, as illustrated in FIG. 15, during operation of the inventive plastic driving mechanism 228.

As can be seen from FIGS. 14 and 15, as cylindrical driving member 209 is rotated, because it is fixed in position within a suitable housing structure, it tends to pull sleeve 213 in a reciprocating motion along the axial direction as illustrated by arrow 217. This reciprocating motion is. coupled to support 219. A drive member 221 is mounted for rotary movement in the directions of arrow 222 on support 219 by a shaft 223. Finally, prophy support 242 is coupled by a shaft 225 to drive member 221. As cylindrical driving member 209 is rotated in the direction indicated by arrow 205, nub 215 is pulled in the directions indicated by arrow 217, resulting in identical movement by the sleeve 213. This reciprocating movement is coupled to shaft 225 causing prophy support 242 and prophy angle 227 to reciprocate in the directions indicated by arrow 229 and achieve the desired action of cleaning the tooth without damage to the gums.

Figure 16:
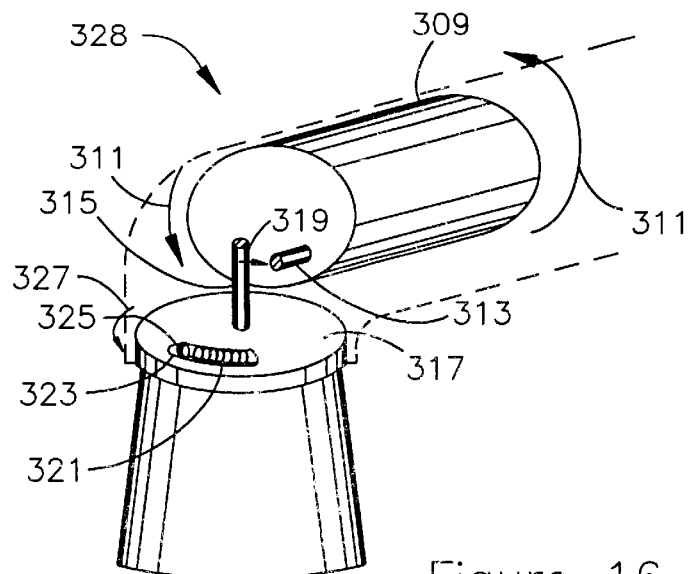
FIG. 16 is a perspective view of a plastic driving mechanism of the dental tool assembly incorporating a cylindrical driving member with shaft.

Referring to FIG. 16, yet another inventive plastic driving mechanism 328 for achieving reciprocating motion in a prophy angle is shown. Generally, in this embodiment, the prophy angle is supported for rotary movement in a housing in much the same manner of the embodiments previously described. Rotary motion is converted into a periodic push which rotates the prophy angle against the prophy support. When the push is released, the prophy angle snaps back into its original position.

More particular, cylindrical driving member 309 is rotated in the direction indicated by arrow 311. Rotation of cylindrical member 309 results in shaft 313 moving in a circular path. Shaft 313 is secured to cylindrical member 309. Periodically, shaft 313 bears against a shaft 315 which is secured to the prophy angle 317.

When shaft 313 bears against shaft 315 on prophy angle 317, it moves shaft 315 and rotates prophy angle 317 in the direction indicated by arrow 319. When this occurs, the spring 321 in a groove 323 in prophy angle 317 is compressed by a stock 325 which is rigidly secured with respect to housing 327 within which the drive member as illustrated in FIG. 16 is contained. As shaft 313 continues to move in a circular path, eventually it is rotated away from shaft 315, releasing shaft 315 and allowing spring 321 to expand, driving prophy angle 317 in the direction of arrow 327, thus resulting in reciprocating movement.

Figure 17:
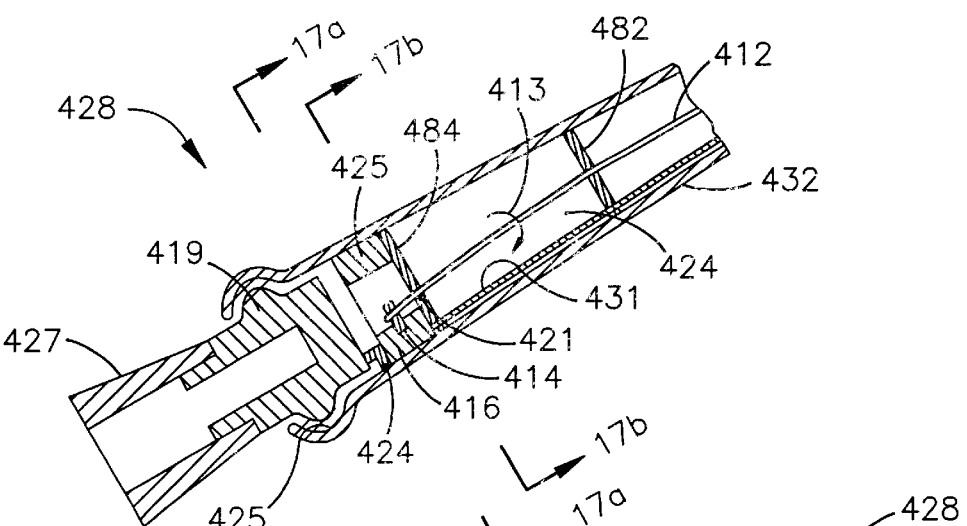
FIG. 17 is a perspective view of a plastic driving mechanism of the dental tool assembly incorporating multiple cam driving mechanism.
Figure 17A:
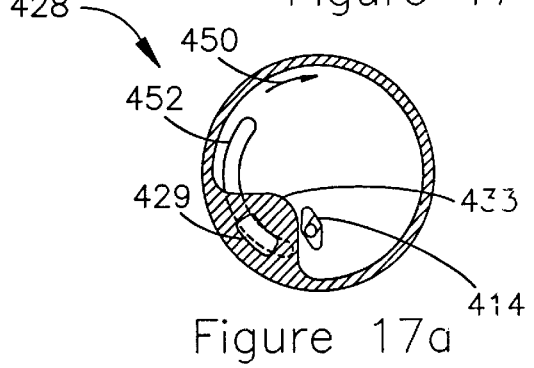
Figure 17B:
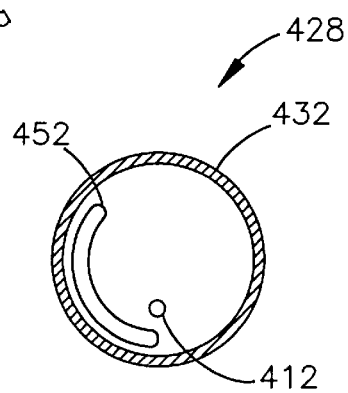

Referring to FIGS. 17a–17c, yet another inventive plastic driving mechanism 428 for achieving reciprocating movement in a prophy angle is illustrated. Here the driving mechanism 428 is driven by a drive shaft 412 with rotary motion in the direction of arrow 413. At the end of drive shaft 412 is a driving cam 414. Drive shaft 412 is retained in position in a space 424 in housing 432 by a disc shaped position retaining element 482 having a centered hole 415 as shown in FIG. 17a, and a second disc shaped position retaining element 484 having an off-centered hole 421 to accept drive shaft 412 as shown in FIG. 17b. The proximal end of drive shaft 412 extends partially through a circumferential shaped driven cam 416 mounted for rotation in housing 432. Prophy angle support 419 can be detachably mounted into housing 432 by an annular ridge 422 Ridge 422 snappingly engages an annular groove 425.

A coupling element 429 connects circumferential shaped driven cam 416 to support 419 in housing 432. A spring like member 431 springingly positions cam 416 in housing 432.

Rotary motion is converted into reciprocating motion when driving shaft 412 rotates, causing the driving cam 414 to bear against circumferential shaped driven cam 416 in the direction as shown by arrow 450. As shown in FIG. 17c, the result is to impart the forward portion of a reciprocating motion to coupling member 429 which is coupled to driven cam 416 and prophy angle support 419. Spring-like member 431, attached to driven cam 416, after a time becomes fully extended, moving in groove 452. When the peak 433 of driven cam 416 is passed by driving cam 414, as shown in dash-dot lines in FIG. 17c, spring-like member 431 springs back causing driven cam 416 to return to its rest position illustrated in solid lines in FIG. 17c. Driving shaft 412 then continues its rotational cycle in the direction of arrow 413 until the pushing and springing back of driven cam 416 is completed.

As driven cam 416 repeatedly returns to its rest position, prophy angle support 419 rotates in the direction indicated by arrow 434, resulting in the desired reciprocating motion of prophy angle 429.

Figure 18:
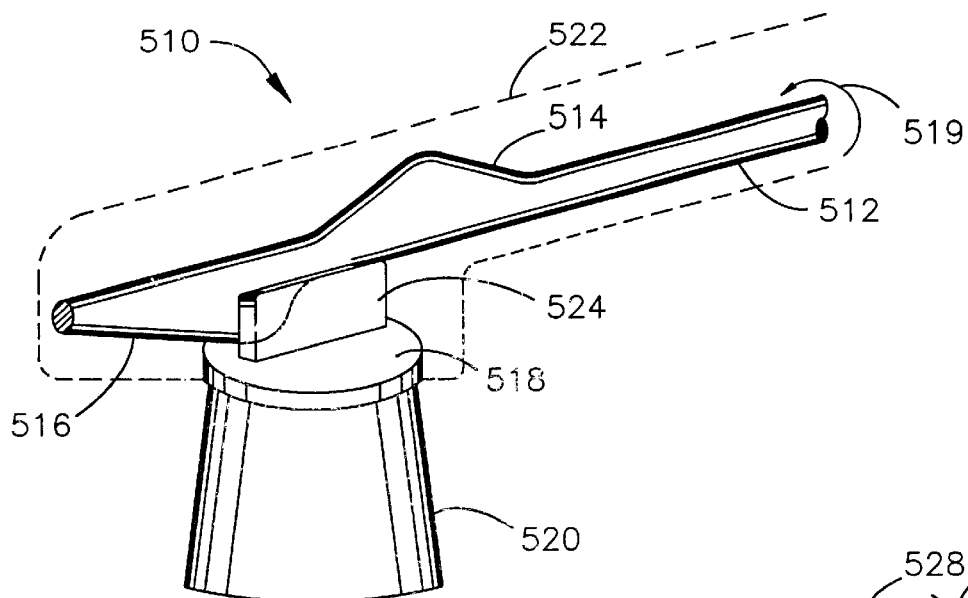
FIG. 18 is a perspective view of a plastic driving mechanism of the dental tool assembly incorporating a lobed member.
Figure 19:
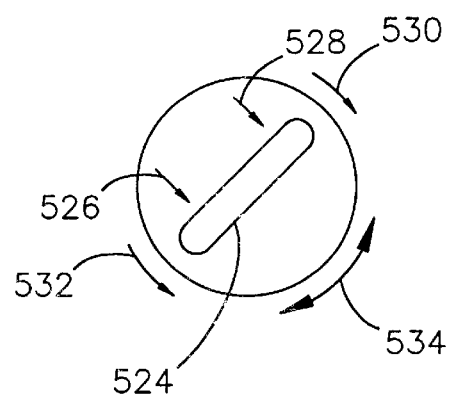
FIG. 19 is a top view of the dental tool assembly of FIG. 18.
Figure 20:
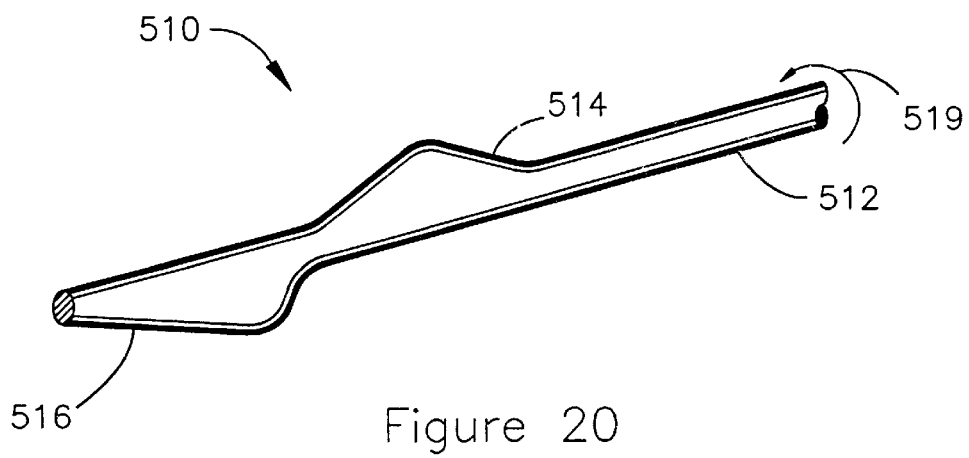
FIG. 20 is a perspective view of the lobed member of FIG. 18.

Turning to FIGS. 18–20, still yet another mechanism for achieving reciprocating movement in a prophy angle is illustrated. In this embodiment, reciprocating motion is achieved in the inventive plastic driving mechanism 510 by applying rotary motion to a lobed member 512. Lobed member 512 includes a pair of lobes 514 and 516. As lobed member 512 rotates in the direction of arrow 519, lobes 514 and 516 follow circular paths but are separated from each other by 180 degrees. In a fashion similar to that of the previous embodiments, a prophy angle support 518 on which a prophy angle 520 is mounted, is supported for reciprocating motion within a housing 522. Prophy angle support 518 includes an elongated cam follower 524 which is alternately acted on by lobe 514 in the direction of arrow 526, and then by lobe 516 in the direction indicated by arrow 528.

More particularly, when lobe 514 bears against elongated cam follower 524, prophy angle support 518 is moved in the direction indicated by arrow 530. Alternatively, when lobe 516 bears against elongated cam follower 524, prophy angle support 518 is moved in the direction indicated by arrow 532. The result of this alternating action is the desired inventive reciprocating motion indicated by arrow 534, as illustrated in FIG. 19.

Figure 21:
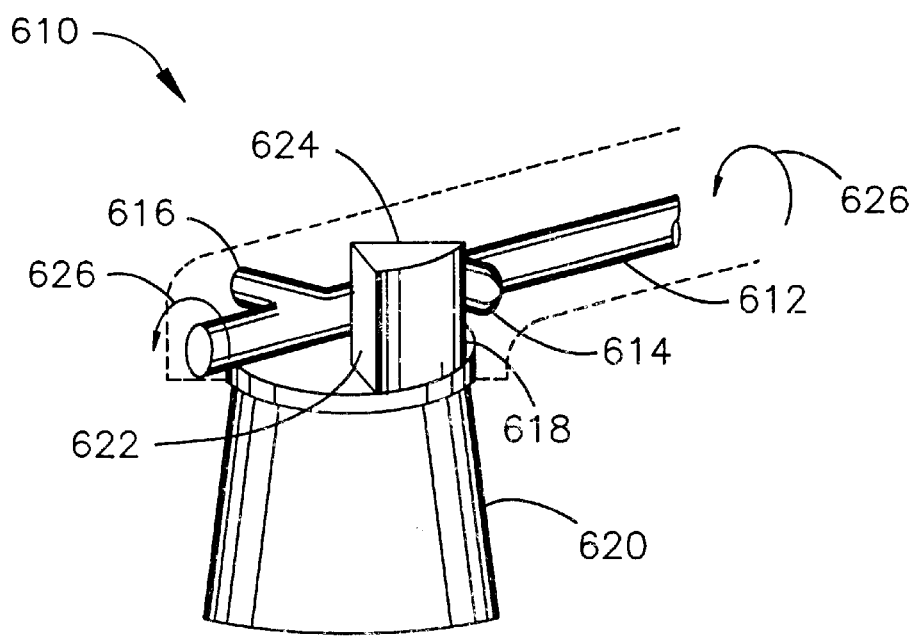
FIG. 21 is a perspective view of a plastic driving mechanism of the dental tool assembly incorporating a wedge-shaped member.
Figure 22:
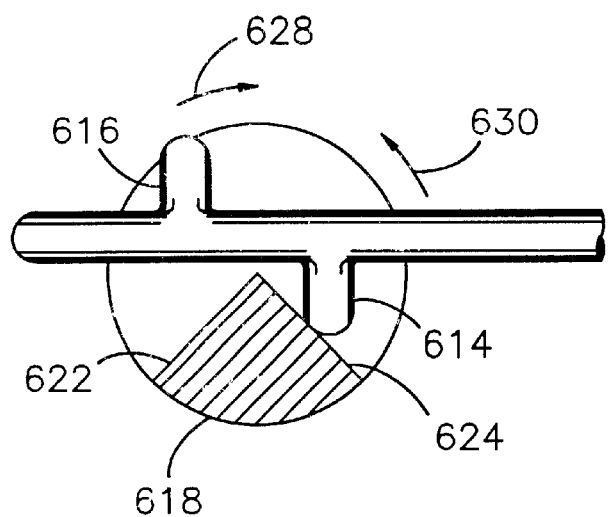
FIG. 22 is a top view of the dental tool assembly of FIG. 21.

Turning to FIGS. 21–22, reciprocating motion is achieved through the use of a wedge-shaped member attached to the prophy support. More particular, the inventive plastic driving mechanism 610 comprises a rotating shaft 612 which has a pair of studs 614 and 616 attached to it. A wedge-shaped member 618 is secured to the top of prophy support 620. Wedge-shaped member 618 includes a pair of side wedge surfaces 622 and 624. As shaft 612 rotates in the direction of arrow 626, alternatively stud 616 bears against surface 624, driving it in the direction of arrow 628, followed by stud 614 bearing against surface 624 driving it in the direction of arrow 630.

Figure 23:
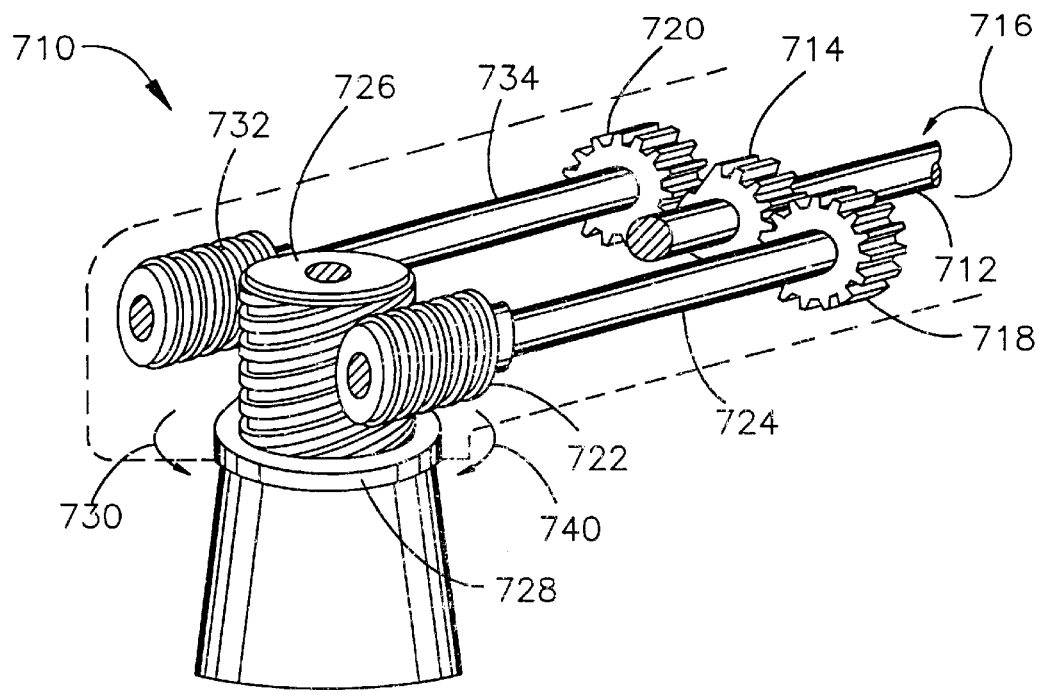
FIG. 23 is a perspective view of a plastic driving mechanism of the dental tool assembly incorporating a multiple gear driving mechanism.
Figure 24:
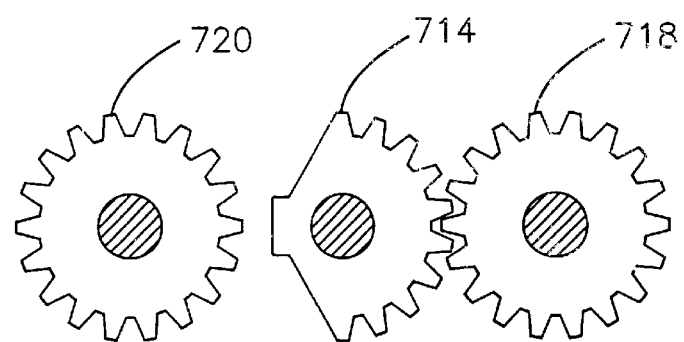
FIG. 24 is a cross-sectional view of the dental tool assembly of FIG. 23 along lines 24 showing the engagement of the driving surfaces of partial gear and follower toothed gears.

In accordance with the present invention, it is also contemplated that gears may be used to achieve reciprocating motion in a dental tool driven by a rotary power source. Referring to FIGS. 23–24, an inventive plastic driving mechanism 710 is provided with an input shaft 712 which is rotated, thus rotating a partial gear 714 which comprises about 75 degrees of a circular gear and has the appearance of a pie slice. As input shaft 712 is rotated in the direction of arrow 716, partial toothed gear 714 alternately engages smaller follower toothed gears 718 and 720 for a short period of time in the overall cycle of rotation of shaft 712.

When follower toothed gear 718 is rotated, it rotates worm gear 722 to which it is attached by coupling shaft 724. This results in worm gear 722 engaging gear 726, causing gear 726 and prophy angle support 728 to which it is secured, to rotate in the direction of arrow 730.

Similarly, when follower toothed gear 720 is rotated, it rotates worm gear 732 to which it is attached by coupling shaft 734. This results in worm gear 732 engaging gear 726, causing gear 726 and prophy angle support 728 to rotate in the direction of arrow 740.

Figure 25:
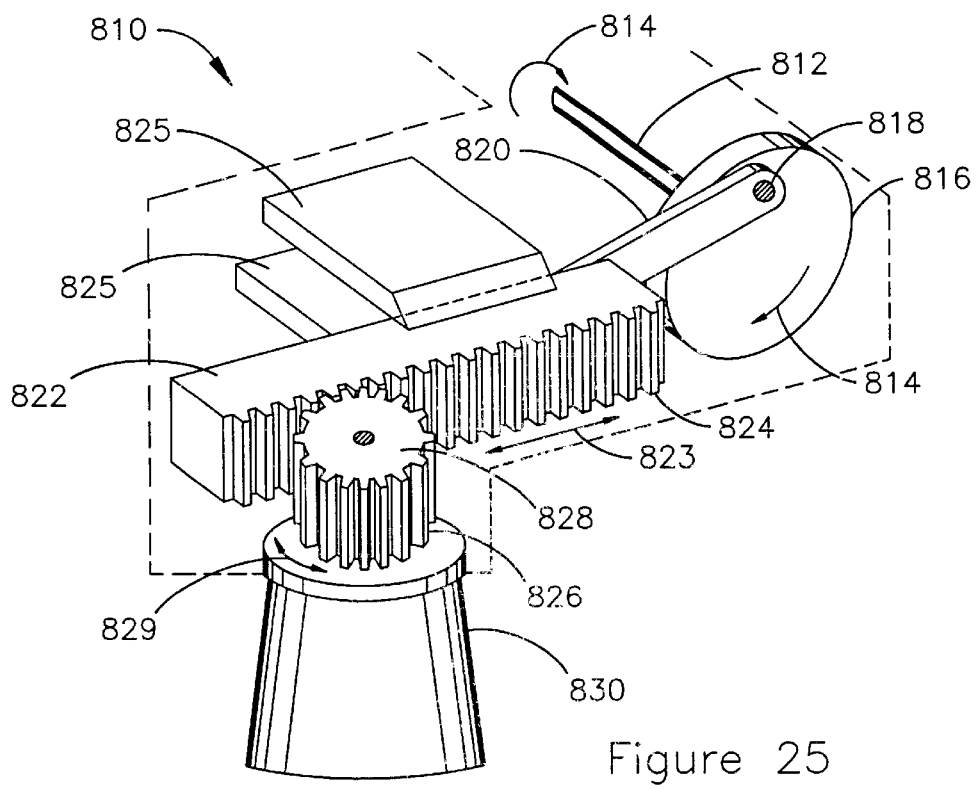
FIG. 25 is a perspective view of a plastic driving mechanism of the dental tool assembly incorporating a rack and pinion driving mechanism.

Referring to FIG. 25, yet another method for achieving the inventive reciprocating motion in a plastic driving mechanism 810 constructed in accordance with the present invention. In accordance with this embodiment, a drive shaft 812 is rotated in the direction indicated by arrow 814. This results in rotating disk 816 in the same direction. A pin 818 is mounted on disk 816. As disk 816 rotates, pin 818 follows a circular path. The result is to impart a reciprocating motion to coupling member 820 which is coupled to a rack 822 having a plurality of teeth 824 on it. Rack 822 is supported for sliding movement in the direction indicated by arrow 823 between a pair of support members 825. In this manner, rack 822 is given a reciprocating motion. Teeth 824 mesh with teeth 826 on pinion 828, causing reciprocating motion in pinion 828. The result is to achieve the desired reciprocating motion as indicated by arrow 829 in prophy angle support 830.

Figure 27:
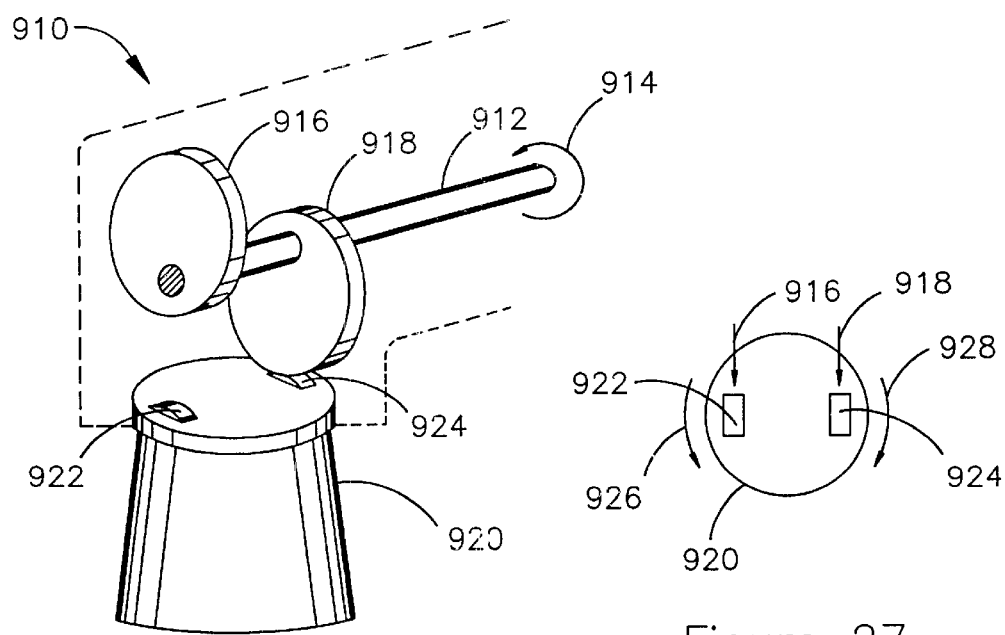
FIG. 27 is a top view of the dental tool assembly in FIG. 26.

Turning next to FIGS. 26 and 27, yet another mechanism for achieving reciprocating motion is shown. Here the inventive reciprocating plastic driving mechanism 910 is driven by a drive shaft 912 with rotary motion in the direction of arrow 914. At the end of drive shaft 912 are a pair of cams 916 and 918. Prophy angle support 920 includes a pair of cams 922 and 924. When cam 916 bears against cam 922 it urges prophy angle support 920 in the direction indicated by arrow 926. Similarly, when cam 918 bears against cam 924 it urges prophy angle support 920 in the direction indicated by arrow 928. Because cams 916 and 918 are positioned on shaft 912 at 180 degrees with respect to each other, they are bearing against cams 922 and 924 at different times, and this causes reciprocating motion in prophy angle support 920.

Still yet another approach is illustrated in FIGS. 28 and 29. In this embodiment, power is provided to the inventive reciprocating plastic driving mechanism 1010 by a drive shaft 1012 which is rotated in the direction of arrow 1014. The end of shaft 1012 has a pair of partial pie-shaped toothed gears 1016 and 1018 which have teeth that mesh with teeth on a conical gear 1020.

As can be seen in FIG. 28, as shaft 1012 rotates, gear 1018 causes follower gear 1020 to rotate in the direction of arrow 1022 when the teeth of gear 1020 engage gear 1018. At other times, when the teeth of gear 1016 engage the teeth of gear 1020, gear 1020 is caused to rotate in the direction indicated by arrow 1024, resulting in reciprocating motion of gear 1020 and prophy angle support 1026.

Referring to FIG. 30, an electromechanical approach to the problem of providing reciprocating motion by an inventive reciprocating plastic driving mechanism 1120 is illustrated. The same may be done using an electromechanical operator 1112 to directly. provide reciprocating motion. Alternatively, a simpler electromechanical operator may be used which only provides for movement in one direction, with movement in the opposite direction being provided by a spring biased arrangement of the type illustrated and described in connection with FIG. 17, above.

Figure 31:
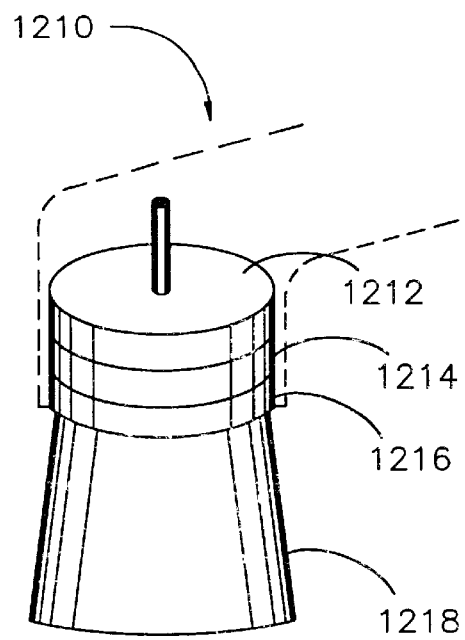
FIG. 31 is a perspective view of a plastic driving mechanism of the dental tool assembly incorporating a magnetic-mechanically coupled multiple clutch driving mechanism.

Turning next to FIG. 31, in accordance with the present invention it is contemplated that magnetic coupling may be used to relieve the stress applied to the gums during continuous motion. Such a magnetic coupling may simply comprise a magnetic clutch. In particular, the inventive reciprocating plastic driving mechanism 1210 is provided with a driving clutch member 1212 which is magnetically coupled to a driven clutch member 1214 to achieve a magnetic-mechanical connection between the two magnet members.

Driving clutch member 1212 and driven clutch member 1214 may also be made of plastic, as such materials are inexpensive and widely available. As alluded to above, the invention contemplates the fabrication of all the embodiments of the invention in plastic, although substitution of other materials is possible. In any case, the inventive structures are conFig.d in a manner that provides for durability, even in relatively inexpensive and weak plastic materials.

When driving clutch member 1212 is rotated, a driven clutch member 1214 is caused to rotate because of the magnetic-mechanical connection, thus resulting in a transfer of power. Clutch member 1214, in turn, is coupled to the prophy angle support 1216 in order to rotate the prophy angle 1218. Such a magnetic clutch will release if tension applied to the gums becomes too great. Such a mechanism can be used in combination with any of the reciprocating plastic driving mechanisms described in this application to achieve an additional measure of protection. In addition, magnetic coupling may be used in place of the various forms of mechanical coupling to achieve the desired reciprocating motion in the various embodiments disclosed herein.

Figure 32:
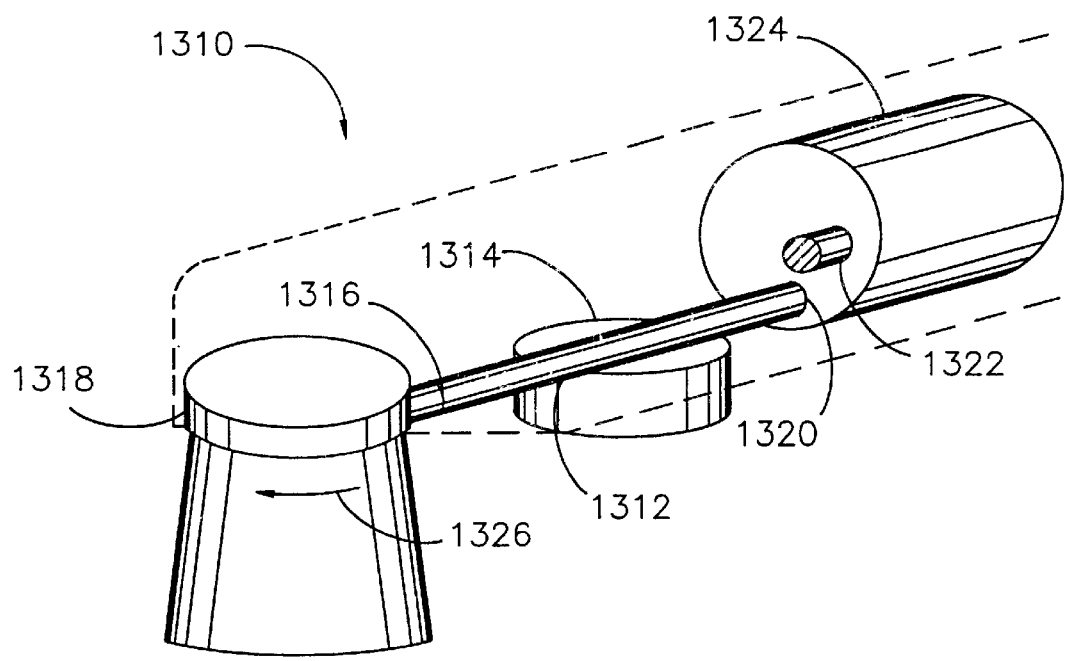
FIG. 32 is a perspective view of a plastic driving mechanism of the dental tool assembly incorporating a spring like driving mechanism.

Turning next to FIG. 32, still yet another approach is illustrated. In accordance with this approach, a reciprocating plastic driving mechanism 1310 includes a plastic spring like member 1312 mounted for rotation on a support 1314 and coupled by a living hinge 1316 to a prophy angle support 1318 as illustrated. The far end 1320 of the spring like member 1312 is acted on by a stud 1322 mounted on a rotating member 1324. When rotating member 1324 rotates, stud 1322 impacts far end 1320, causing the other end to displace the position of living hinge 1316 causing movement of prophy angle support 1318 in the direction indicated by arrow 1326. Because member 1312 is a spring, when the impact is over, prophy angle support 1318 moves in the opposite direction, thus resulting in reciprocating motion.

Figure 33:
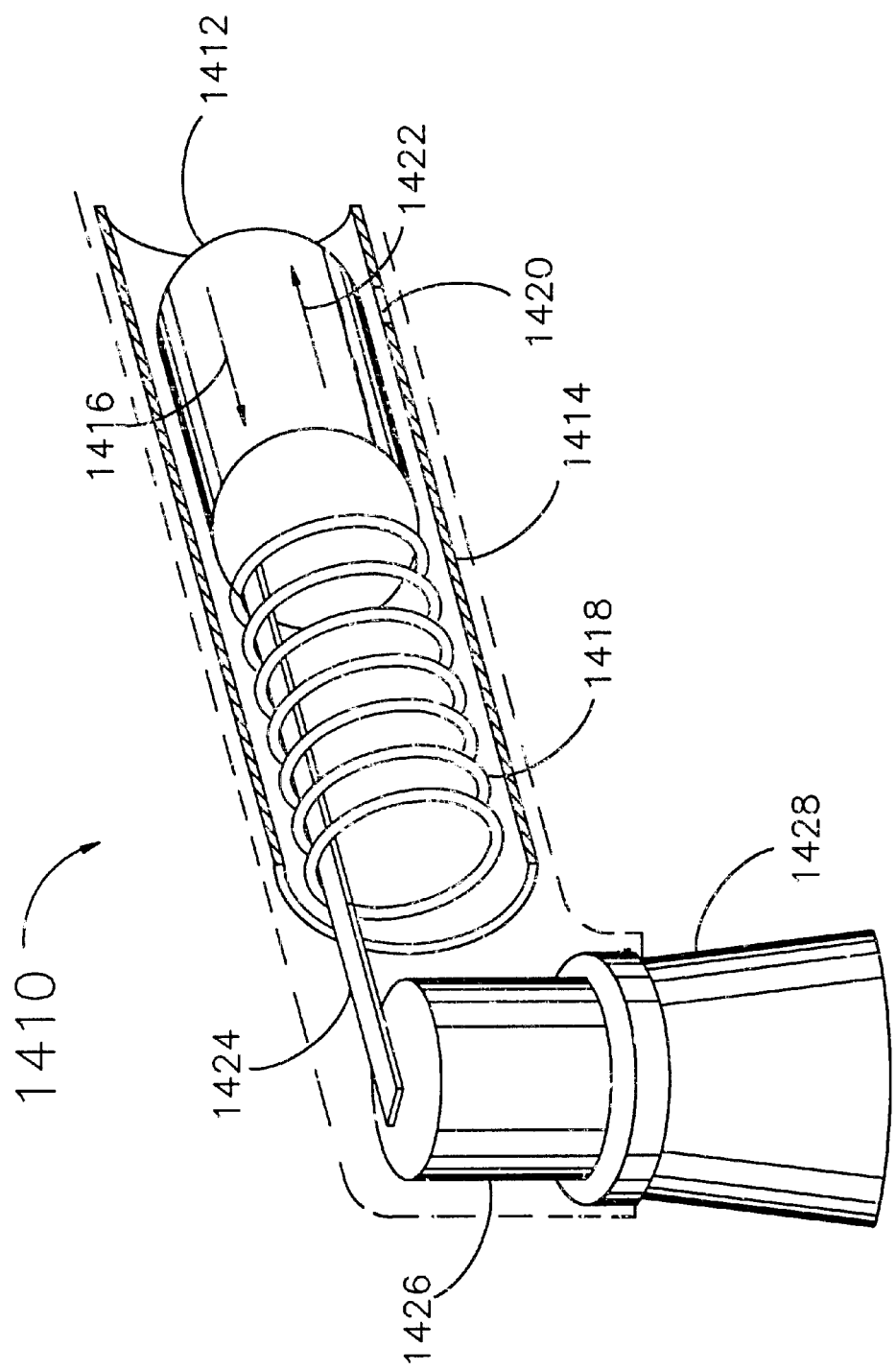
FIG. 33 is a perspective view of a plastic driving mechanism of the dental tool assembly incorporating a piston driving mechanism.

Turning to FIG. 33, because dental tools often have air pressure as a primary source of power, and it is this air pressure which is used to drive a dentist's drill, using a converter which converts air pressure into rotary motion, the possibility also exists to achieve reciprocating motion from air pressure directly. The same can be achieved in a reciprocating plastic driving mechanism 1410 by a number of means, including the use of a piston 1412 in a cylinder 1414. The air pressure drives the piston 1412 in the direction indicated by arrow 1416 against the action of a spring 1418 which is compressed by the movement of the piston 1412. Pressure maybe released by a vent 1420 causing spring 1418 to push the piston 1412 back in the direction indicated by arrow 1422. Piston 1412 is coupled by link 1424 to a prophy angle support 1426. The result is that link 1424 couples the reciprocating motion to prophy angle support 1426 resulting in reciprocating motion of prophy angle 1428.

Figure 34:
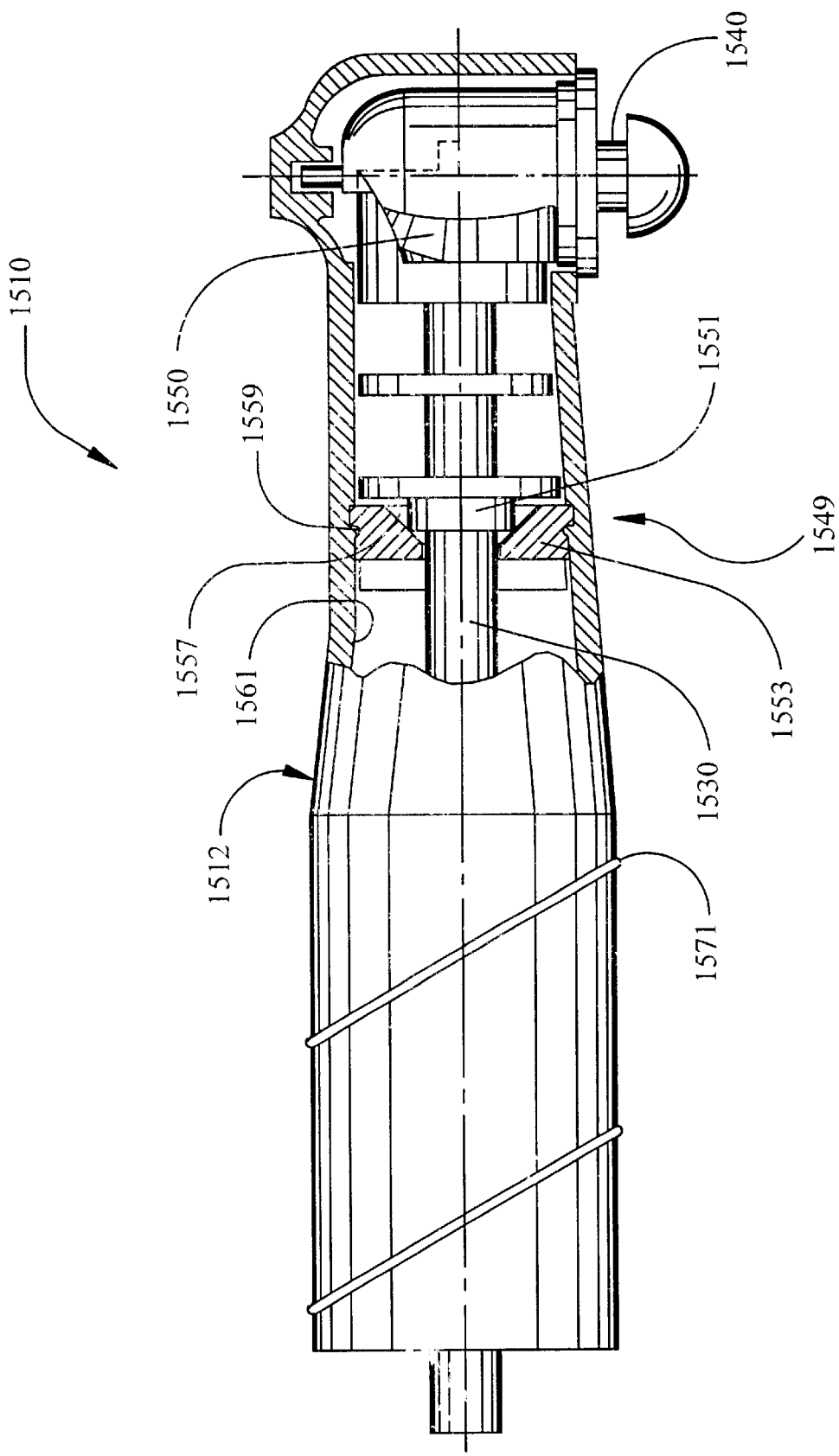
FIG. 34 is a view like FIG. 1 showing an alternative embodiment of a bearing assembly for rotational support of a drive shaft of the drive mechanism.

Referring to FIG. 34, an alternative embodiment for providing longitudinal axial positioning is provided. This embodiment also provides an alternative means of assembling dental tool assembly 1510. A bearing assembly 1549 includes a bearing journal 1551 and a bushing 1553 that cooperate in holding drive shaft 1530 in axial alignment holding drive surface 1550 and driven surface 1560 in contact with each other. Bushing 1553 is held in position within housing 1512 by means of a snap-fit arrangement. This embodiment replaces stop flange 80 and latch 86, as shown in FIG. 1.

Figure 35:
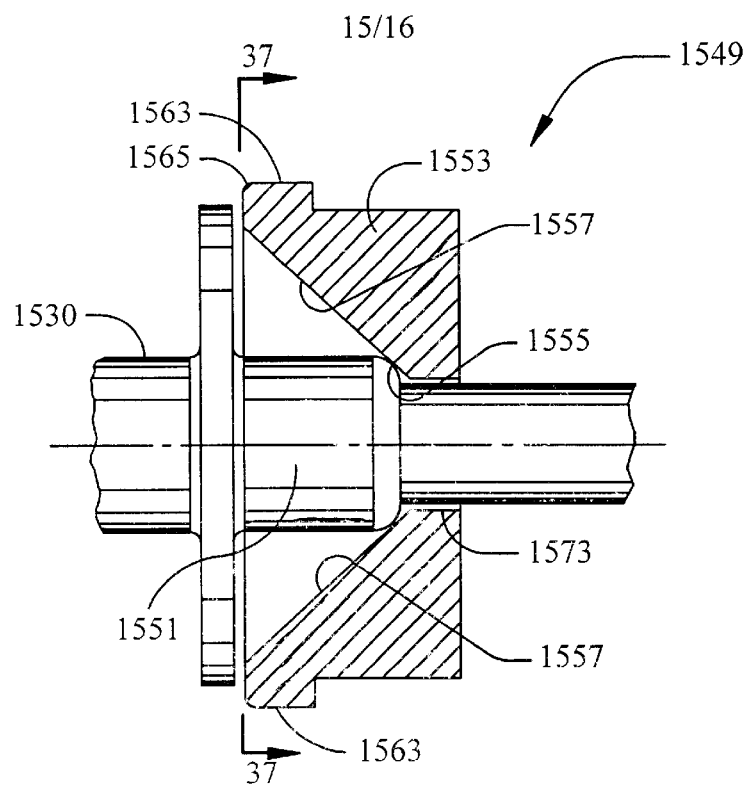
FIG. 35 is an enlarged view, partially in section, showing a bushing and its journal on a drive shaft.
Figure 36:
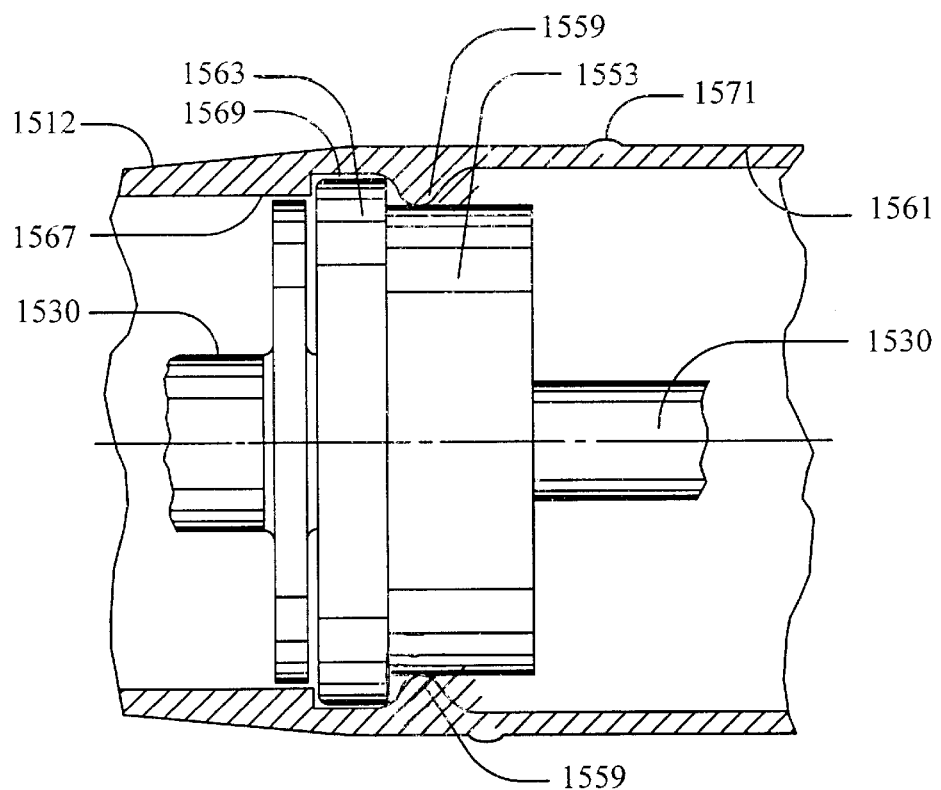
FIG. 36 is a view similar to FIG. 35 including a housing shown in section for illustrating a snap-fit arrangement of the bushing in the housing.
Figure 37:
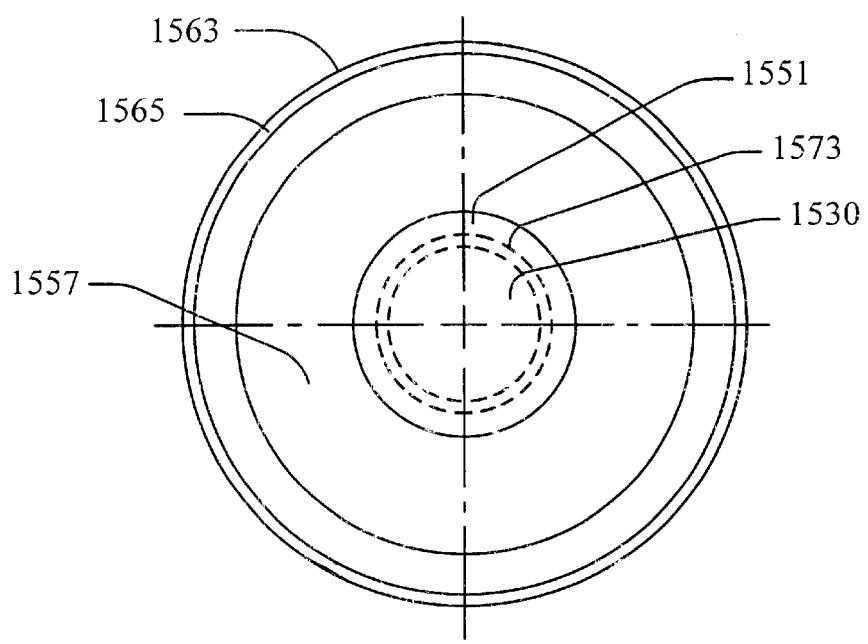
FIG. 37 is an axial view of the bearing assembly taken along line 37—37 of FIG. 34.
Figure 37A:
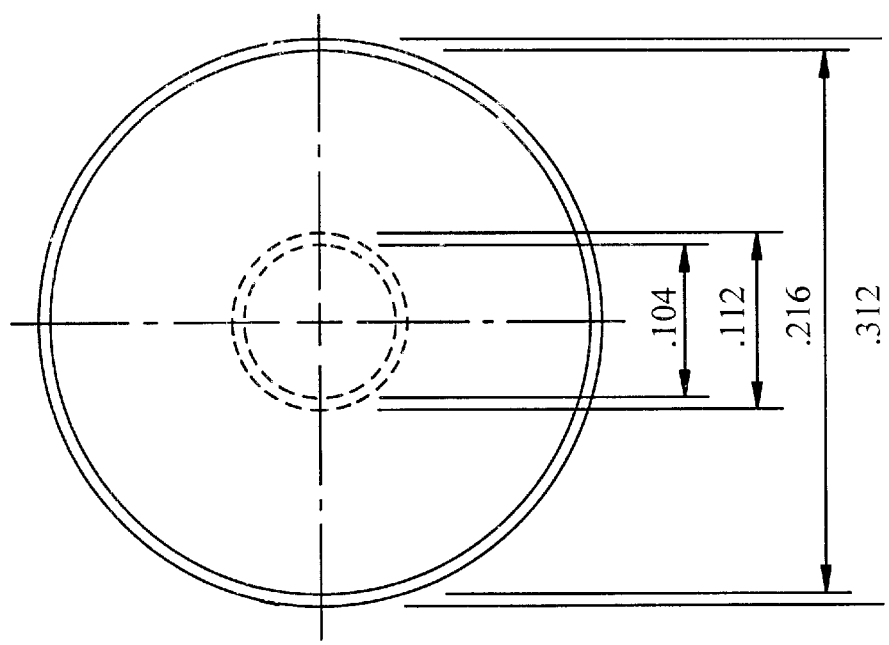

Referring now to FIGS. 35 to 37, the relationship between drive shaft 1530, journal 1551, and bushing 1553 is shown, with bushing 1553 being shown in section. Drive shaft 1530 includes a bearing journal 1551 having an outside diameter greater than the outside diameter of drive shaft 1530. Bearing journal 1551 may be integral with drive shaft 1530 or formed separately and attached to drive shaft 1530 by any suitable means. Journal 1551 includes a rearward contact surface 1555 part of which forms a contact area with bushing 1553. Surface 1555 may be any shape, preferably in an appropriate shape to reduce friction and increase reliability. Bushing 1553 is generally disk-shaped and has an inwardly facing frustoconical surface 1557. frustoconical surface 1557 has intrinsic characteristics in this configuration. Surface 1557 aids in centering drive shaft 1530 as it passes through bushing 1553 and also promotes a snug fit without being overly tight while simultaneously reducing the contact surface area with journal contact surface 1555, all desirable characteristics. At the same time, bushing 1553 presents a very simple configuration that is readily produced, especially in plastic.

Referring now to FIG. 36, bearing assembly 1549 is shown in position within housing 1512 which is shown in section. For retaining bushing 1553 in position, a retaining structure on its periphery includes a ridge 1559 extending radially inwardly from an inside wall 1561 of housing 1512. Ridge 1559 is preferably integral with housing 1512 and may be any suitable shape but is preferably radiased. In order to ensure that bushing 1553 is held firmly in position a collar 1563 extends radially outwardly from bushing 1553 and is preferably integral therewith. The inside diameter of ridge 1559 is preferably less than the outer diameter of collar 1563 thereby forming an interference fit between the two forming what is commonly referred to as a snap-fit. The snap-fit arrangement described above is only one possible arrangement and similar arrangements are also contemplated by the present invention. By way of example and not limitation, a reduced diameter area in the outer diameter of bushing 1553 could be used to form a snap-fit arrangement with ridge 1559. In order to aid the preferred arrangement during assembly a chamfer 1565 is formed on an a leading edge of outer diameter of bushing 1553. Housing 1512 may include a reduced diameter section 1567 at the point where bushing 1553 is to be positioned. A receiving area 1569 formed between ridge 1559 and reduced diameter section is sized to receive collar 1563. The arrangement described above holds bushing 1553 in place which in turn holds drive shaft 1530 in place acting through journal 1551 for normal operation of dental tool assembly 1510.

Housing 1512 also includes a raised portion 1571 extending outwardly from its outer surface and is preferably integral therewith. Raised portion 1571 is sized and positioned to aid a user in gripping dental tool assembly 1510, which may include a single or multiple spiral arrangement.

Bearing assembly 1549 as described above has additional benefits in that it greatly simplifies assembly of dental tool assembly 1510. During assembly, driven shaft 1540 is properly positioned within housing 1512 and then drive shaft 1530 is inserted into housing 1512 in its proper position. Bushing 1553 is then introduced to the open end of housing 1512 with drive shaft 1530 sliding through a central aperture 1573 of bushing 1553. The fit between bushing 1553 and drive shaft 1530 is preferably toleranced so as to minimize contact between the two components yet allow for a minimal increase in diameter of drive shaft 1530 to form journal 1551 thereon. Once inserted into the end of housing 1512 bushing 1553 is then pushed down into its final position with the snap-fit occurring at the end of insertion. This then holds drive shaft 1530 and driven shaft 1540 in reasonably permanent position within housing 1512 which is the in use position for dental toll assembly 1510.

While the foregoing description and drawings represent the preferred embodiments of the present invention, it will be understood that various additions, modifications and substitutions may be made without departing from the spirit and scope of the present invention as defined in the accompanying claims. In particular, it will be clear that the present invention may be embodied in other specific forms, structures, arrangements, proportions, and with other elements, materials, and components, without departing from the spirit or essential characteristics thereof.

For example, although housing 12 is in the form of a prophy angle, driving mechanism 28 may be used in any other desired dental tool assembly, or any other motorized device that requires oscillating rotary motion of an output end. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A bearing assembly for a disposable prophy angle drive mechanism that includes a housing, a drive shaft and a driven shaft, said bearing assembly comprising:
   a bushing, said bushing having an aperture dimensioned to receive said drive shaft of said drive mechanism, said bushing also having an inwardly facing frustoconical shaped surface; and
   a journal located along said drive shaft, said journal having a contact surface sized and positioned to contact said frustoconical shaped surface of said bushing, said journal and said bushing positioned within said prophy angle drive mechanism to minimize axial movement of said drive shaft within said prophy angle drive mechanism.

2. A bearing assembly according to claim 1, wherein said bushing has an outside diameter sized to fit within said housing and includes a retaining structure.

3. A bearing assembly according to claim 2, wherein said retaining structure is a snap-fit arrangement.

4. A bearing assembly according to claim 3, wherein said snap-fit arrangement includes a collar-extending radially outwardly from said bushing and a ridge extending radially inwardly from an inside surface of said housing where said collar has an outside diameter greater than an inside diameter of said ridge.

5. A bearing assembly according to claim 4, wherein said collar is integral with said bushing and said ridge is integral with said housing.

6. The improved drive mechanism of claim 3, wherein said snap fit arrangement includes a ridge extending radially outwardly from an outer peripheral surface of said bearing and a groove within a housing for said dental tool assembly with said ridge being larger in diameter than an internal diameter of said housing such that said ridge snaps into position within said groove when pushed into alignment therewith.

7. A bearing assembly according to claim 1, wherein a retaining structure is integral with said bushing and said housing.

8. A bearing assembly according to claim 1, wherein said journal is integral with said drive shaft.

9. The improved drive mechanism of claim 8, further including a snap fit arrangement integral with said housing and holding said frustoconical bearing surface in position to act as a thrust bearing for said drive shaft holding it in position relative to said driven shaft.

10. A bearing assembly according to claim 1, wherein said journal has a contact surface shaped to minimize contact area with said frustoconical surface.

11. A bearing assembly according claim 1, said bearing assembly comprising: a bushing, said bushing having an aperture sized to receive a drive shaft of said drive mechanism, said bushing also having a snap-fit arrangement on its outer periphery that cooperates with a mating arrangement of said prophy angle drive mechanism.

12. An improved driving mechanism for a dental tool assembly where the driving mechanism includes a housing, a drive shaft having a rotation axis and a drive surface, a driven shaft having a rotation axis and a driven surface, the drive shaft and the driven shaft are positioned with respect to each other such that the rotation axis of the drive shaft is transverse to the rotation axis of the driven shaft and the drive surface and driven surface are in contact such that the drive and driven surfaces cooperate with each other causing oscillation of the driven shaft about its rotation axis and the drive surface and driven surface are each curved such that the drive surface and the driven surface are in continuous contact upon rotation of said drive shaft about said rotation axis of said drive shaft said drive surface is substantially conical and said conical drive surface has a cone axis that is at an approximately 45° angle with respect to said rotation axis of said drive shaft and a transverse surface portion that is at an approximately 90° angle with respect to said rotation axis, said improvement comprising;
   a bearing having a frustoconical bearing surface and an aperture sized and positioned to receive said drive shaft; and
   a journal, said journal being integral with said drive shaft and sized and positioned to contact said frustoconical bearing surface thereby acting as a thrust bearing holding said drive shaft in position within said housing.

13. A transmission for changing rotary motion into angularly reciprocating motion and adapted to be mounted on the output end of a dental power unit of the type having a rotary drive output and used to drive a dental tool, said transmission comprising:

(a) a support member;

(b) a driving member in a first plane oriented in a first direction supported by said support member for rotary motion;

(c) a driven member made of a resinous material and supported by said support member for reciprocating angular movement by said support member in a second plane, said second plane being transverse to said first plane, said driving member, said driven resinous member and said support member forming a transmission subassembly adapted to be mounted on the output end of said dental power unit with said rotary drive output mechanically coupled to said driving member;

(d) a driving cam surface disposed on a portion of said driving member, said driving cam surface having a first shape;

(e) a driven cam surface disposed on a portion of said driven resinous member, said driven cam surface having a second shape, said driven resinous member being supported with respect said driving member in a position where said driving cam surface is in contact with said driven cam surface during at least a portion of the cycle of rotation of said driving cam surface, said second shape configured and dimensioned to be driven by said driving cam surface in a positive angular direction during one part of said cycle and be driven by said driving cam surface in a negative angular direction during another part of said cycle.

* * * * *